(12) United States Patent
Shulz et al.

(10) Patent No.: US 9,904,258 B2
(45) Date of Patent: Feb. 27, 2018

(54) TESTING MACHINE WITH GRAPHICAL USER INTERFACE WITH SITUATIONAL AWARENESS

(71) Applicant: MTS Systems Corporation, Eden Prairie, MN (US)

(72) Inventors: Bradley Dean Shulz, Savage, MN (US); Michael Ray Buth, Chanhassen, MN (US); Jeffrey Allan Breece, Davison, MI (US); David Martin Tillman, Mound, MN (US); Maureen Bitney, Minnetonka, MN (US); Darrell Robert Bennington, Eden Prairie, MN (US); Pinkiekumar D. Patel, Eden Prairie, MN (US)

(73) Assignee: MTS SYSTEMS CORPORATION, Eden Prairie, MN (US)

( * ) Notice: Subject to any disclaimer, the term of this patent is extended or adjusted under 35 U.S.C. 154(b) by 581 days.

(21) Appl. No.: 13/842,993

(22) Filed: Mar. 15, 2013

(65) Prior Publication Data

US 2014/0142759 A1    May 22, 2014

Related U.S. Application Data

(60) Provisional application No. 61/649,363, filed on May 20, 2012.

(51) Int. Cl.
*G05B 15/02* (2006.01)
*G05B 17/02* (2006.01)
(Continued)

(52) U.S. Cl.
CPC ............... *G05B 15/02* (2013.01); *G01N 3/08* (2013.01); *G05B 17/02* (2013.01); *G05B 23/0216* (2013.01)

(58) Field of Classification Search
CPC .......... G01N 3/08; G05B 15/02; G05B 17/02; G05B 23/0216
(Continued)

(56) References Cited

U.S. PATENT DOCUMENTS

| 6,023,980 | A  | * | 2/2000 | Owen et al. ............ 73/797 |
| 6,311,149 | B1 | * | 10/2001 | Ryan ............ G06F 11/2294 |
| | | | | 703/21 |
| 6,879,926 | B2 | | 4/2005 | Schmit |
| 7,089,803 | B1 | | 8/2006 | Scoville |

(Continued)

FOREIGN PATENT DOCUMENTS

GB    2431484 A    4/2007

OTHER PUBLICATIONS

International Search Report and Written opinion dated Feb. 18, 2014 for corresponding International Patent application No. PCT/US2013/041839 filed on May 20, 2013.

*Primary Examiner* — Yuhui R Pan
(74) *Attorney, Agent, or Firm* — Steven M. Koehler; Westman, Champlin & Koehler, P.A.

(57) ABSTRACT

A testing machine for testing a test specimen includes an actuator assembly configured to be coupled to the test specimen; and a computing device configured to control the actuator assembly, the computing device including a graphical user interface that renders at least a visual representation or a simulated visual representation of at least a parameter of the component or the component changing in accordance with changes of the actual corresponding component on the testing machine.

25 Claims, 26 Drawing Sheets

(51) Int. Cl.
*G05B 23/02* (2006.01)
*G01N 3/08* (2006.01)

(58) Field of Classification Search
USPC .................................. 700/275; 715/792, 839
See application file for complete search history.

(56) References Cited

U.S. PATENT DOCUMENTS

| | | |
|---|---|---|
| 7,168,077 B2 | 1/2007 | Kim |
| 7,200,529 B2 | 4/2007 | Cifra |
| 7,366,993 B2 | 4/2008 | Joffrain |
| 7,496,480 B2 | 2/2009 | Pasquarette |
| 7,650,589 B2 | 1/2010 | Cifra |
| 2004/0153350 A1 | 8/2004 | Kim |
| 2004/0158812 A1 | 8/2004 | Dye |
| 2005/0035966 A1 | 2/2005 | Pasquarette |
| 2005/0039160 A1 | 2/2005 | Santori |
| 2005/0096872 A1 | 5/2005 | Blevins |
| 2005/0288913 A1* | 12/2005 | Shah ................ G06F 17/5022 703/14 |
| 2006/0277010 A1 | 12/2006 | Shcutte et al. |
| 2007/0005159 A1* | 1/2007 | Borah et al. .................... 700/83 |
| 2007/0118237 A1 | 5/2007 | Wang |
| 2008/0046784 A1 | 2/2008 | Gygi |
| 2008/0077530 A1 | 3/2008 | Banas |
| 2009/0222699 A1 | 9/2009 | Abbott |
| 2010/0077260 A1* | 3/2010 | Pillai et al. ..................... 714/46 |
| 2013/0042696 A1* | 2/2013 | Fukuda ................... G01N 3/04 73/800 |
| 2013/0066613 A1* | 3/2013 | Russell ................. G05B 17/02 703/7 |

* cited by examiner

TESTING MACHINE WITH GRAPHICAL USER INTERFACE WITH SITUATIONAL AWARENESS

CROSS-REFERENCE TO RELATED APPLICATION

The present application is based on and claims the benefit of U.S. provisional patent application Ser. No. 61/649,363, filed May 20, 2012, the content of which is hereby incorporated by reference in its entirety.

BACKGROUND

The discussion below is merely provided for general background information and is not intended to be used as an aid in determining the scope of the claimed subject matter.

Test machines or apparatus are used to test parameters and/or performance of materials, components, consumer products, electronics, materials, as well as medical and other devices (i.e. test specimens). Typically, test machines include one or more actuators to apply input loads and displacement. Illustrative actuators include hydraulic actuators as well as electrically driven actuators. Operation of the actuators is computer controlled; however, at least some of the steps necessary to setup the test machine for testing a test specimen and/or ascertaining a parameter or condition of the test machine are not intuitive.

SUMMARY

This Summary and the Abstract are provided to introduce a selection of concepts in a simplified form that are further described below in the Detailed Description. This Summary, the Abstract and the Detailed Description are not intended to identify key features or essential features that must be included in any embodiment of the invention, nor are they intended to be used as an aid in determining the scope of the claimed subject matter. A first aspect of the present invention is testing machine for testing a test specimen that includes an actuator assembly configured to be coupled to the test specimen; and a computing device configured to control the actuator assembly, the computing device including a graphical user interface that renders at least a visual representation or a simulated visual representation of at least a parameter of the component or the component changing in accordance with changes of the actual corresponding component on the testing machine.

A second aspect of the present invention is a testing machine for testing a test specimen that includes an actuator assembly configured to be coupled to the test specimen; and a computing device configured to control the actuator assembly, the computing device including a graphical user interface rendering at least a visual representation or a simulated visual representation of the testing machine, the graphical user interface having a second portion spaced apart from the first portion, the second portion listing a plurality of tasks for configuring the testing machine, wherein performance of at least some tasks by the user graphically changes visual representation or the simulated visual representation.

A third aspect is a testing machine having an actuator; a fixture configured to enagage a test specimen to conduct a test; and a controller configured to control the actuator, the controller configured to access a storage device having information related to operating parameters of the actuator, and information related to operating parameters of the fixture, the controller having a graphical user interface to visually render relative location of the parameters of the fixture with respect to the location of the parameters of the actuator.

DETAILED DESCRIPTION OF ILLUSTRATIVE EMBODIMENTS

Setup and/or operation of a testing machine at least some of the time has been cumbersome and generally time-consuming. At a minimum, this has limited the ability for users of the test machine to efficiently conduct tests. The embodiments of the present disclosure address and solve these concerns, at least in part, by providing a system utilizing a graphical user interface (GUI) and a processor coupled to the GUI and configured to cause the GUI to graphically display elements and/or parameters of the testing machine 12 in an intuitive manner, and/or allow the user to adjust parameters of the testing machine in an intuitive manner.

Figure 1:
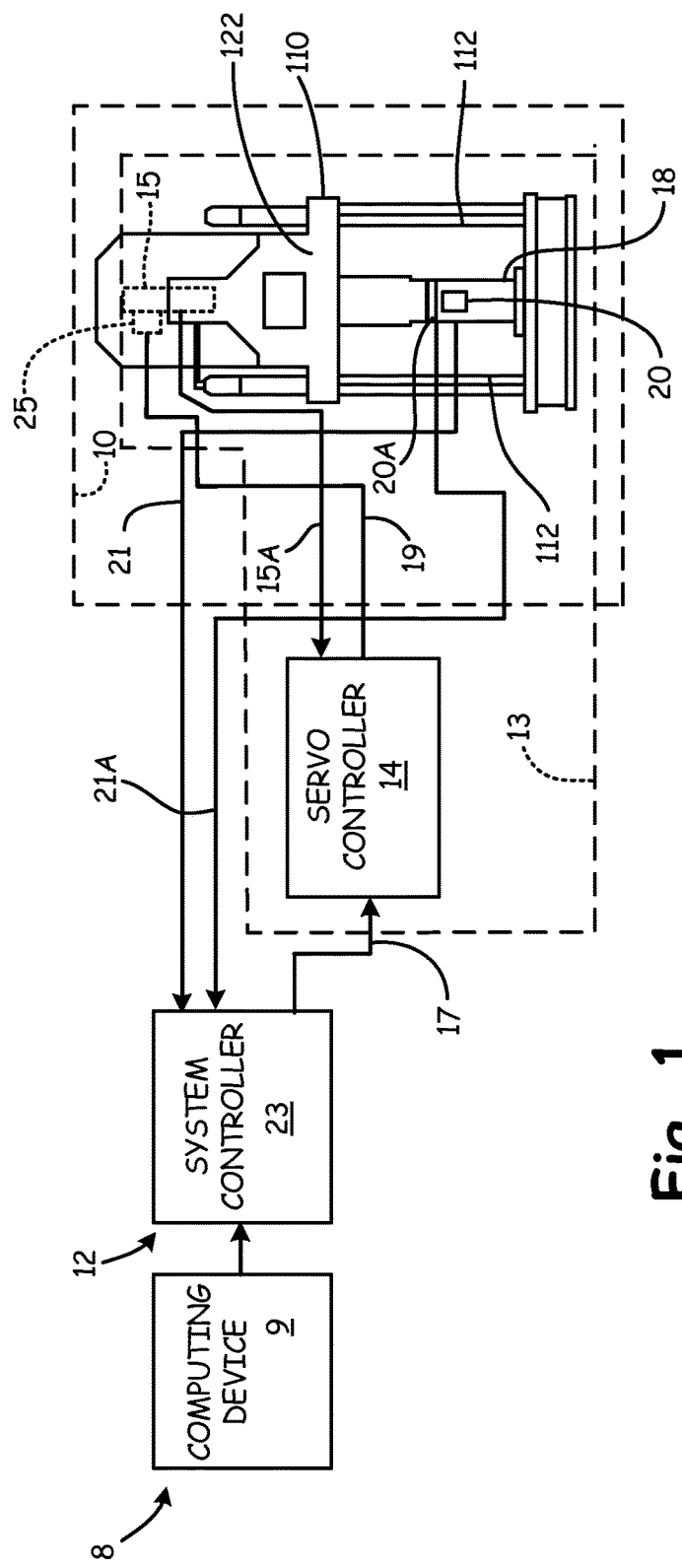
FIG. 1 is a schematic illustration of a process control loop for controlling operation of a test apparatus.

FIG. 1 illustrates a testing machine system 8 comprising a computing device 9 for generating a GUI 47 (FIG. 2) that more intuitively allows a user to interact and/or control a test machine 12. Test machine 12 includes a plant or physical system 10. In the exemplary embodiment, the physical system 10 generally includes a controllable element such as an actuator system, motor or the like. As illustrated in FIG. 1, the actuator system or assembly 13 includes a controller 14 and an actuator 15 (hydraulic, pneumatic and/or electric) and mechanisms coupling actuators to any moveable member for imparting displacements or loads upon a test specimen 18.

In the schematic illustration of FIG. 1, the actuator system 13 is represented by actuator 15 that in turn represents one or more actuators in any test machine 12 that are coupled to the test specimen 18 directly or indirectly. The controller 14 provides an actuator command signal 19 to a controlled device 25 (e.g. servo valve, power controller) to operate the actuator 15, which in turn, excites the test specimen 18. It should be noted the controller 14 is of a design suitable for controlling the type of actuator employed. Suitable feedback 15A can be provided from the actuator 15 to the controller 14 or from other sensors. One or more remote transducers 20 on the test specimen 18 or physical system 10, such as displacement sensors, strain gauges, accelerometers, load cells, thermometers or the like, provide a measured or actual response 21. In the exemplary embodiment, a load cell 20A also provides a response 21A. A system controller 23 receives actual response 21 as feedback in a response to a drive 17 as input to the servo controller 14. In the illustration of FIG. 1, signal 17 is a reference signal, signal 19 is a manipulated variable (command to actuated device) and signal 15A is a feedback variable. Although illustrated in FIG. 1 for the single channel case, multiple channel embodiments with signal 15A comprising N feedback components and the signal 19 comprising M manipulated variable components are typical and considered another embodiment of the present invention. The test specimen 18 can take any number of forms such as but not limited to material samples, substructures or components. Typically, types of loads that can be applied or imparted to the test specimen 18 include tension, compression and/or torsion in one or more degrees of freedom applied separately or at the same time. The test specimen 18 can also or alternatively be subjected to controlled displacements in one or more degrees of freedom applied separately or at the same time.

Figure 2:
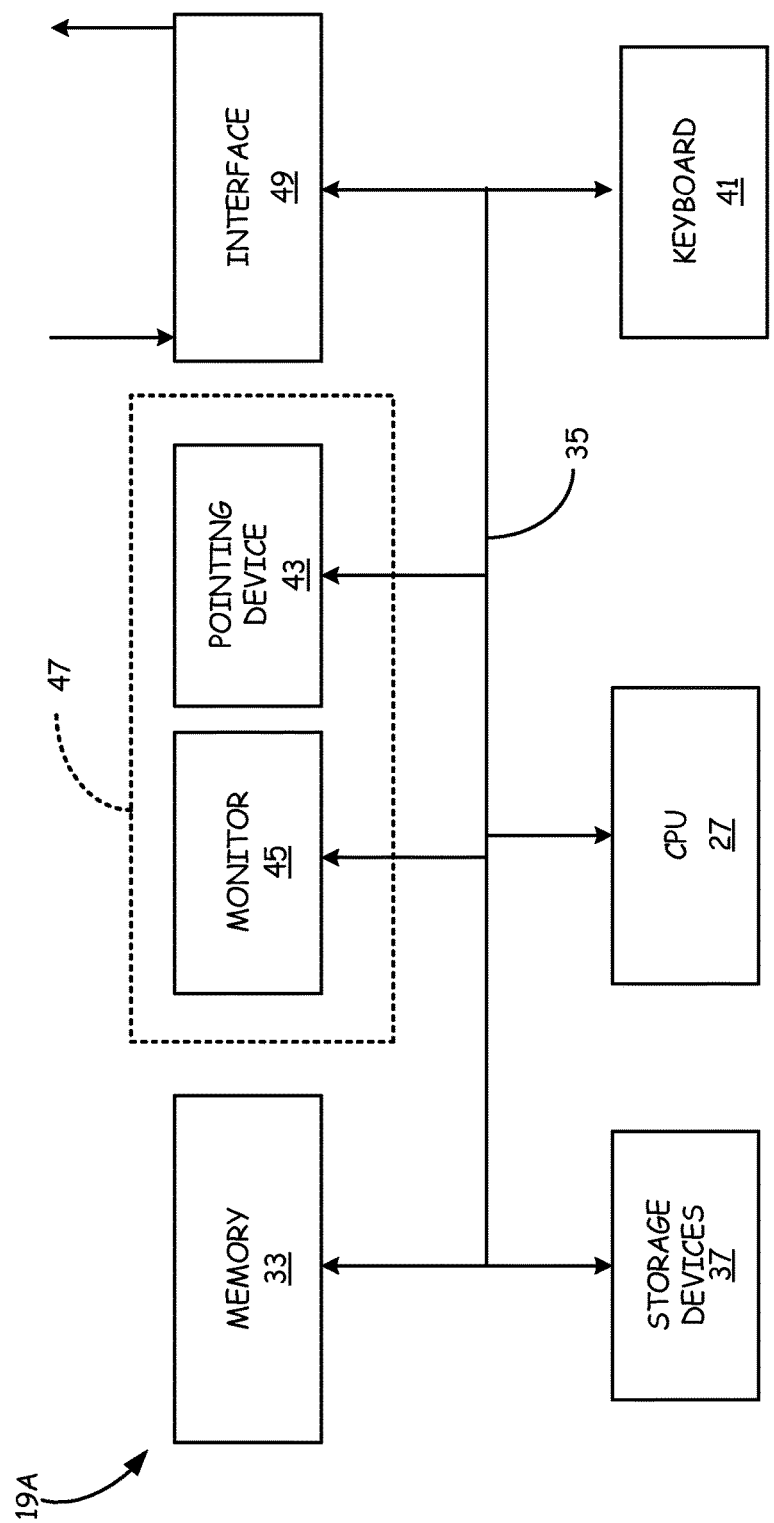
FIG. 2 is a block diagram depicting certain components of a computing device.

The computing device 9, controller 14 and system controller 23 can each be implemented on a digital and/or analog computer. FIG. 2 and the related discussion provide a brief, general description of a suitable computing environment in which the computing device 9, controller 14 and system controller 23 may each be implemented. Although not required, the test computing device 9 will be described, at least in part, in the general context of computer-executable instructions, such as program modules, being executed by a computer 19A. Generally, program modules include routine programs, objects, components, data structures, etc., which perform particular tasks or implement particular abstract data types. Those skilled in the art can implement the description below and/or block diagrams to computer-executable instructions storable on a computer readable medium. Moreover, those skilled in the art will appreciate that the invention may be practiced with other computer system configurations, including multi-processor systems, networked personal computers, mini computers, main frame computers, and the like. Aspects of the invention may also be practiced in distributed computing environments where tasks are performed by remote processing devices that are linked through a communications network. In a distributed computer environment, program modules may be located in both local and remote memory storage devices.

The computer 19A illustrated in FIG. 2 comprises a conventional computer having a central processing unit (CPU) 27, memory 33 and a system bus 35, which couples various system components, including memory 33 to the CPU 27. System bus 35 may be any of several types of bus structures including a memory bus or a memory controller, a peripheral bus, and a local bus using any of a variety of bus architectures. The memory 33 includes read only memory (ROM) and random access memory (RAM). A basic input/output (BIOS) containing the basic routine that helps to transfer information between elements within the computer 19A, such as during start-up, is stored in ROM. Storage devices 37, such as a hard disk, a floppy disk drive, an optical disk drive, etc., are coupled to the system bus 35 and are used for storage of programs and data. It should be appreciated by those skilled in the art that other types of computer readable media that are accessible by a computer, such as magnetic cassettes, flash memory cards, digital video disks, random access memories, read only memories, and the like, may also be used as storage devices. Commonly, programs are loaded into memory 33 from at least one of the storage devices 37 with or without accompanying data.

Input devices such as a keyboard 41 and pointing device (mouse) 43, or the like, allow the user to provide commands to the computer 19A. A monitor 45 or other type of output device is further connected to the system bus 35 via a suitable interface and provides feedback to the user. If the monitor 45 is a touch screen, the pointing device 43 can be incorporated therewith. The monitor 45 and typically an input pointing device 43 such as mouse together with corresponding software drivers form a graphical user interface (GUI) 47 for computer 19A that is particularly useful with aspects described below.

Interfaces 49 on each of the computing device 9 and system controller 23 allow communication between the computing device 9 and the system controller 23. Likewise, interfaces 49 on each of the system controller 23 and the controller 14 allow communication between the system controller 23 and the controller 14. Interface 49 also represents circuitry used to send signals 19 or receive signals 15 and 21 as described above as well as other parameters of the physical system such as the status of locks, doors, indicators, whether power is applied, etc. Commonly, such circuitry comprises digital-to-analog (D/A) and analog-to-digital (A/D) converters as is well known in the art. The controller 14 can also comprise an analog controller with or without digital supervision as is well known. Functions of computing device 9, controller 23 and controller 14 can be combined into one computer system. In another computing environment, controller 14 is a single board computer operable on a network bus of another computer, which could be controller 23 or another supervisory computer. The schematic diagram of FIG. 2 is intended to generally represent a computer for these and other suitable computing environments.

Figure 3:
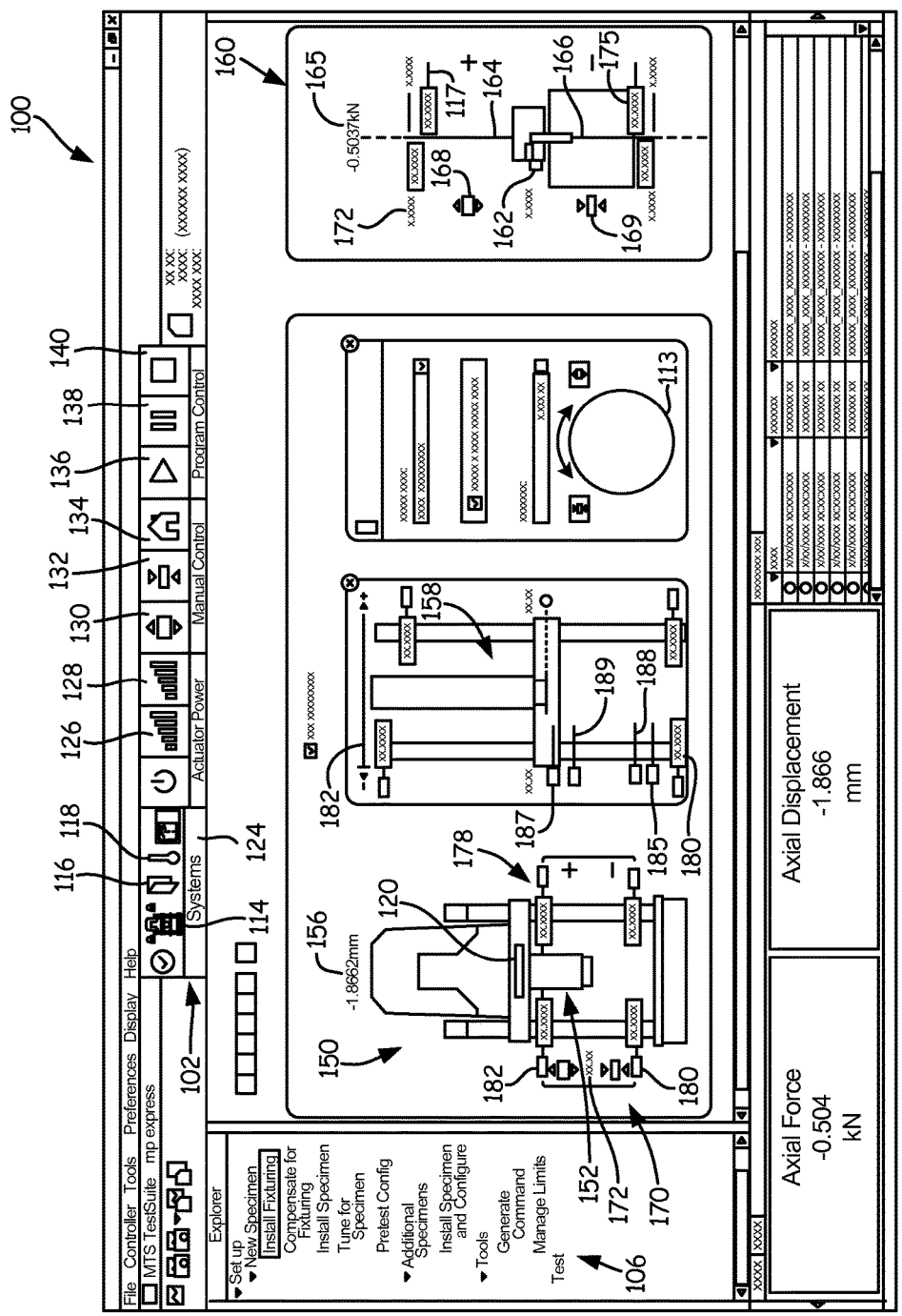
FIGS. 3-7 illustrate exemplary screen shots from a graphical user interface (GUI) during the creation of a test flow, employing presently disclosed embodiments.

FIG. 3 illustrates generally GUI 47 rendering graphical image 100 on a suitable display where a user using a pointing device such as a mouse, pen or even just even a finger (if the display includes a touch sensitive screen) interacts with the graphical image 100 to set or adjust parameters of the test machine 12 (which can also be stored in system controller 23 or controller 14) and/or control the test machine 12 generally. One aspect of the GUI 47 is that it provides situational awareness to the user of the state of the testing machine 12 or parameters thereof. Generally, the image 100 includes a plurality of panels or display portions 102, 104 and 106 each with specific purpose. Portion 102 includes icons indicative of the state of the testing machine 12. Portion 106 allows the user to select different general tasks to perform with the testing machine 12 the details of which are not pertinent to the aspects of the present invention unless as discussed below. For example, a detailed discussion of limits as provided by GUI 47 is described below where some or all of limit management can be accessed under the category "Manage Limits". Portion 104 is a main display area, the images of which as well as the type and extent of user interaction functionality will vary depending on the category selected in portion 106.

In the exemplary embodiment of FIG. 1, the testing machine 12 includes a crosshead 110 that is movable on vertical columns 112, Locks selectively clamp the crosshead 110 to the vertical columns 112 so as to provide a rigid reaction structure. Position sensors monitor the actual state of each of the locks and provides a corresponding output signal, the status of which is communicated to computing device 9. Icon 114 indicates the state of the locks for the crosshead 110 that being whether they are locked or unlocked.

Reiterating that the embodiment of FIG. 1 is merely exemplary. In yet a further embodiment, the actuator assembly 13 can operatively couple one or more actuators to the crosshead 110, the movement of which imparts loads on the test specimen 18 in the alternative, or in addition to actuator 15. Therefore, a testing machine as used herein and the actuator assembly 13 can include various forms of couplers, links, bell cranks and the like.

In yet a further embodiment, the position of the cross head 110 can be measured and a corresponding input provided to computing device 9 whereat the position of the cross head 110 (i.e. head assembly) is represented by GUI 47 relative to its position for example with respect to the vertical columns 112. This is particularly advantageous for the user can understand the work space available between the cross head 110 and the base. In addition, by monitoring the position of the cross head 110 the computing device 9 can provide warnings if operational limits are reached statically or dynamically during configuration, or testing. If desired, the locations of the cross head 110 can be stored sequentially during repositioning thereof so as to allow the cross head 110 to be returned to a previous location.

In some applications the testing machine 12 is disposed within an enclosure, typically, at least partially transparent. A position sensor monitors the actual state of the door of the enclosure and provides a corresponding output signal, the status of which is communicated to computing device 9. Icon 116 indicates whether the door to the enclosure is open or closed.

Various components such as the actuator system 13 may heat up during use. Temperature sensor(s) can be provided to monitor the temperature of such components and provide a corresponding output signal, the status of which is communicated to computing device 9. Icon 118 provides an indication of the temperature of the monitored component.

Indicator 120 is of similar shape to an indicator light 122 (FIG. 1) provided on the testing machine 12. Indicator 120 changes color, blinks, etc. in the same fashion as the indicator light 122 so as to indicate the operational state of the testing machine 12.

Icon 124 indicates whether the testing machine 12 is powered up. In addition, icon 124 also comprises a button on the GUI which can be activated by the user using the pointing device to turn power on or off, although in a preferred embodiment the user can use icon 124 to turn power off. Typically, another power switch is physically provided on or near the testing machine 12 that can also turn power on or off. Icon 124 provides the current state if the other switch is activated.

Icons 126 128, which also function as buttons, indicate the relative power or performance available from the actuator system 13. Icon/button 126 is used to limit the available power, velocity, or other performance parameter of the actuator system 13, which may be desirable during test specimen setup or verification, while icon/button 128 allows increased or maximum power, velocity or other performance parameters of the actuator system 13.

Buttons 130, 132 and 134 adjust the position of the actuator rod of the actuator 15, and hence allows the actuator rod to be raised, lowered or returned to a preselected "home" position, respectively.

Buttons 136, 138 and 140 allow a test procedure previously selected or defined to "run", "paused" or "stopped," respectively. Like icon/button 124, any or all of buttons 126, 128, 130, 132 and 134 are commonly provided on another user interface, typically, proximate or part of the actual testing machine 12. Hence, the user can use either the GUI portion 102 or the other interface to control the testing machine 12. Other simulated visual representations of actual buttons, knobs, sliders, switches on testing machine 12 can be represented in image 100 where such simulated visual representations can be manipulated by the pointing device to perform the same function as the actual button, knob, slider, switch, etc. it represents. An example, is provided in FIG. 3 where simulated visual representation 113 of a dial corresponds to an actual dial on the testing machine 12. It should be noted herein "simulated visual representation" is not a photograph of the item; rather it is of a form of a computer graphic.

Display portion 104 allows the user to visually see typically a simulated visual representation 150 of the testing machine 12, and more importantly, a simulated visual representation 150 of the position of the actuator rod within its operable range. In other words, the simulated visual representation 150 of the actuator rod relative to the simulated visual representation 150 of the testing machine 12 (or to a scale 170 disposed proximate the simulated visual representation 150) corresponds to the actual position of the actuator rod of the actuator 15. The simulated visual representation 152 of the actuator rod intuitively allows the user to understand the state or position of the actuator rod since it is graphically displayed in a manner that mimics or represents its actual state or position. Commonly, the position of the actuator rod is indicated to the user with a numerical value, which is also provided in portion 104 at 156, however, misinterpreting or misreading the numerical value if that is all that is provided as in the prior art can cause further problems that can, for instance, cause damage to the test specimen. Simulated visual representation 150 of the actuator rod provides the user an intuitive indication that can help avert such problems.

Referring to FIG. 3, in another embodiment, portion 104 can upon selection by the user through activation of an appropriate button, include an enlarged simulated visual representation 158 of the actuator rod relative to scale 170 or a portion thereof. The scale 170 or portion thereof can have a static range, or, if desired, be based on the position of the actuator rod where upper and lower values vary depending on the position of the actuator rod. If due to the test being performed or to be performed, the total displacement of the actuator rod is quite small, the GUI, if desired, can automatically display the enlarged simulated visual representation 158.

At this point, it should be noted that the simulated visual representation 150, 158 of the actuator rod, may not have direct correspondence to the actual position of the actuator rod, when the actuator rod is moving during a test procedure such as during testing of a test specimen. This is particularly the case during oscillatory movement of the actuator rod at rates hard to visually perceive. In such cases, the simulated visual representation 150, 158 can be altered to mimic oscillatory movement at a frequency that may not correspond to the actual frequency of movement. In another embodiment, the actual oscillatory movement of the actuator rod may be indicated by some other simulated visual representation, including a static simulated visual representation of the actuator rod (or end thereof), that does not try to mimic oscillatory movement, for instance, by indicating the extent of the range of movement of the actuator rod. However, for operating states of the actuating system 13 where the actual actuator rod is stationary or moving at a relatively slow rate of speed, the GUI simulated visual representation 150, 158 thereof preferably corresponds to the actual position.

In another embodiment, a photograph or visual representation of a testing machine can be used along with a simulated visual representation of the scale 170 and simulated visual representation of associated limits. In other words, in another embodiment, motion of the actuator rod is not provided.

If desired, the GUI 11 can provide a simulated visual representation of a load applied by the actuating system 13.

Referring to FIG. 3, a simulated visual representation of the load applied is indicated at 160. Simulated visual representation 160 can include a visual representation (simulated or actual photograph) of a load cell 162 with, in the exemplary embodiment illustrated, indicator portions 164, 166 extending in directions away from load cell image 162 that represents the direction of the force applied, exemplified herein as being parallel to extension/retraction of the simulated visual representation 150 of the actuator rod. Indicator portions 164 can visually change to indicate the amount of load being applied such as a length of color change (or including a movable indicator) relative to a simulated visual representation of a scale 166. Indicator portions representing the direction and amount of force being applied can take other forms than that illustrated. For instance, the graphical indications of force being applied can be disposed anywhere adjacent the load cell visual representation 162 such as above or below or to the side thereof. A numerical indicator of load applied can be provided such as at 165. In the embodiment illustrated, icons 168 and 169 can be provided to represent tension and compression, respectively. As described above with respect to simulated visual representation 150, 158, simulated visual representation 160 of load applied corresponds to actual load being applied in static or relatively slowly changing operating states; however, in oscillatory operating states at higher frequencies, the simulated visual representation 160 may not have direct correspondence to the actual load being applied at any given instance, but rather in a dynamic or static representation visually indicate that the oscillatory load is being applied.

At this point it should be noted that the GUI 47 is not limited to only simulated visual representations of actuator rod displacement and/or application of load. Rather, GUI 47 can include other parameters related to the test machine 12, the test specimen 18, or of a sensor for the test specimen 18. For instance, in addition to or in the alternative, a simulated visual representation of velocity (See FIG. 5 at 119) and/or acceleration of the movement of the actuator rod can be displayed relative to a suitable scale, for instance, in a manner similar to displacement or load as described above. Likewise, in addition or in the alternative, a parameter of the test specimen can be visually represented on the GUI 47. For example, an extensometer may be operably coupled to the test specimen, the output signal of which can be monitored and visually represented on the GUI 47, preferably relative to a scale, to show extension and/or compression (See FIG. 5 at 123). Other parameters such as temperature of a test environment and/or of the test specimen can be monitored and visually represented, for instance relative to a scale, as well as have portions enlarged in a manner similar to displacement discussed above, if needed or desired (See FIG. 5 at 121). These are but some examples of simulated visual representations that can be provided by GUI 47, the list of which should not be considered exhaustive. However, it should be noted GUI 47 can display actual photographic images of some components, particularly, when simulated movement of a portion of the component is not rendered. As indicated above, an actual photograph can comprise the visual representation of the load cell 162. Likewise, an actual photograph of an extensometer can comprise the visual representation of the extensometer that is rendered. However, if the photographic image of an item is manipulated to simulate motion, then the photographic image having simulated motion is a "simulated visual representation" as used herein.

It should be noted that GUI can include absolute and/or relative scales. Referring to FIG. 3, scale 170 is an absolute scale indicative of actuator rod position where opposite ends of scale 170 indicated the extent of displacement one way or the other. If desired, the scale 170 can be relative to an intermediate point representing zero such as but not limited to a midpoint indicated at 172. If desired, the scale 170 need not have an intermediate zero point but instead be arranged to increase in one direction or the other.

GUI 47 can also have a relative scale such as indicated at 178 that takes into account an offset from that of the absolute scale 170. The offset being generated, for example, but not limited to from mass connected to the load cell depicted that in effect changes where zero load is established.

Figure 7:
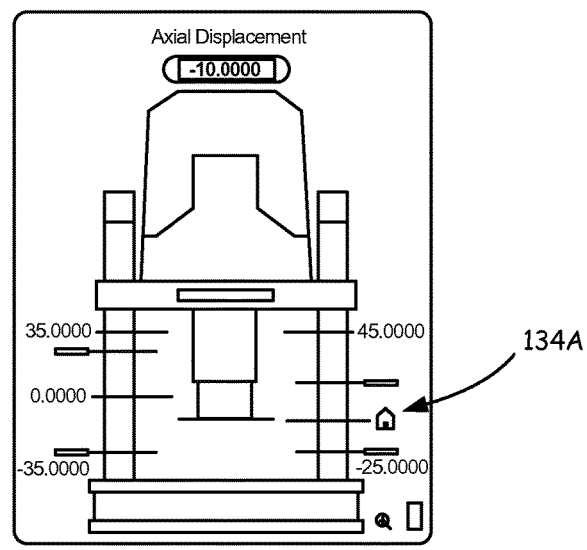

If desired, a simulated visual representation 134A of the "home" position of the actuator rod can be illustrated relative to the absolute scale 170 and/or relative scale 178 as illustrated in FIG. 7. This intuitively enables the user to understand where the "home" position has been assigned and thus where the actuator rod will return to if the "home" icon 134 is activated.

Another aspect of GUI 47 is the simulated visual representation of limits and, if possible and/or desired, adjustment of the simulated visual representation of limits. The simulated visual representations of limits correspond to actual limit values stored in the controller 14, system controller 23 or other monitoring system on testing machine 12. Referring to FIG. 3 and the absolute scale 170 simulated visual representation of system limits are indicated at 180 and 182. System limits 180, 182 indicate the absolute limit of motion of the actuator rod of actuator 15. Typically, system limits, such as limits 180 and 182 for displacement, are not moveable or adjustable by the user and are often set at the factory, or by a factory technician during a retrofit if the actual component to which the system limits pertain is replaced with a similar actual component having a different operating range. It should be noted that in other scenarios, system limits may be entered by the user, or automatically by the test machine 12, during a retrofit if the retrofit is performed by the user.

Along with the simulated visual representation of the system limits 180, 182, the user may be able to assign an action that is initiated by the testing machine 12, controller 14 and/or system controller 23. Commonly, if during operation of the testing machine 12, a system limit 180 or 182 is detected, there is an action that is automatically undertaken by the testing machine 12 to avoid damage to the testing machine 12, or components thereof. If the system limits pertain to actuator rod displacement such as do limits 180 or 182, the testing machine 12, controller 14 and/or system controller 23 will stop further motion of the actuator rod by controlling it in some manner such as initiating a stop command, although actions can also include shutting off power to the actuating system 13. The specific action taken to avoid damage to the testing machine 12 upon reaching a system limit 180, 182 is not an aspect of the present invention and will vary depending on the component to which the system limits pertain. If desired, the user through the GUI 47 can assign other actions to also be taken, for instance by selecting such action from a pull down menu 183 (FIG. 4) displayed proximate the limit and associated therewith. Other actions but not limited to can be for the actuator 15 to apply a selected force or move to a selected position. For instance, the additional action can be to send or initiate a notification message to the user that a limit has been reached or activated. Advantageously, when a limit has been reached a simulated visual representation can be shown to the user clearly indicating which limit has been reached. The simulated visual representation can be a change in the limit icon or another indicator can be provided along side the limit that has been reached.

As discussed above, the scale 170 can be any parameter of the testing machine 12, test specimen 18 or sensor used to measure a parameter of the test specimen 18. For instance, the system limits can be the operating range of an environmental chamber such as the temperature thereof. Another example is the system limits can be the operating range of an extensometer attached to the test specimen. Simulated visual representation of load as measured by a load cell can include "system" or "component" limits 184, 186 of the load cell in the testing machine 12.

Figure 4:
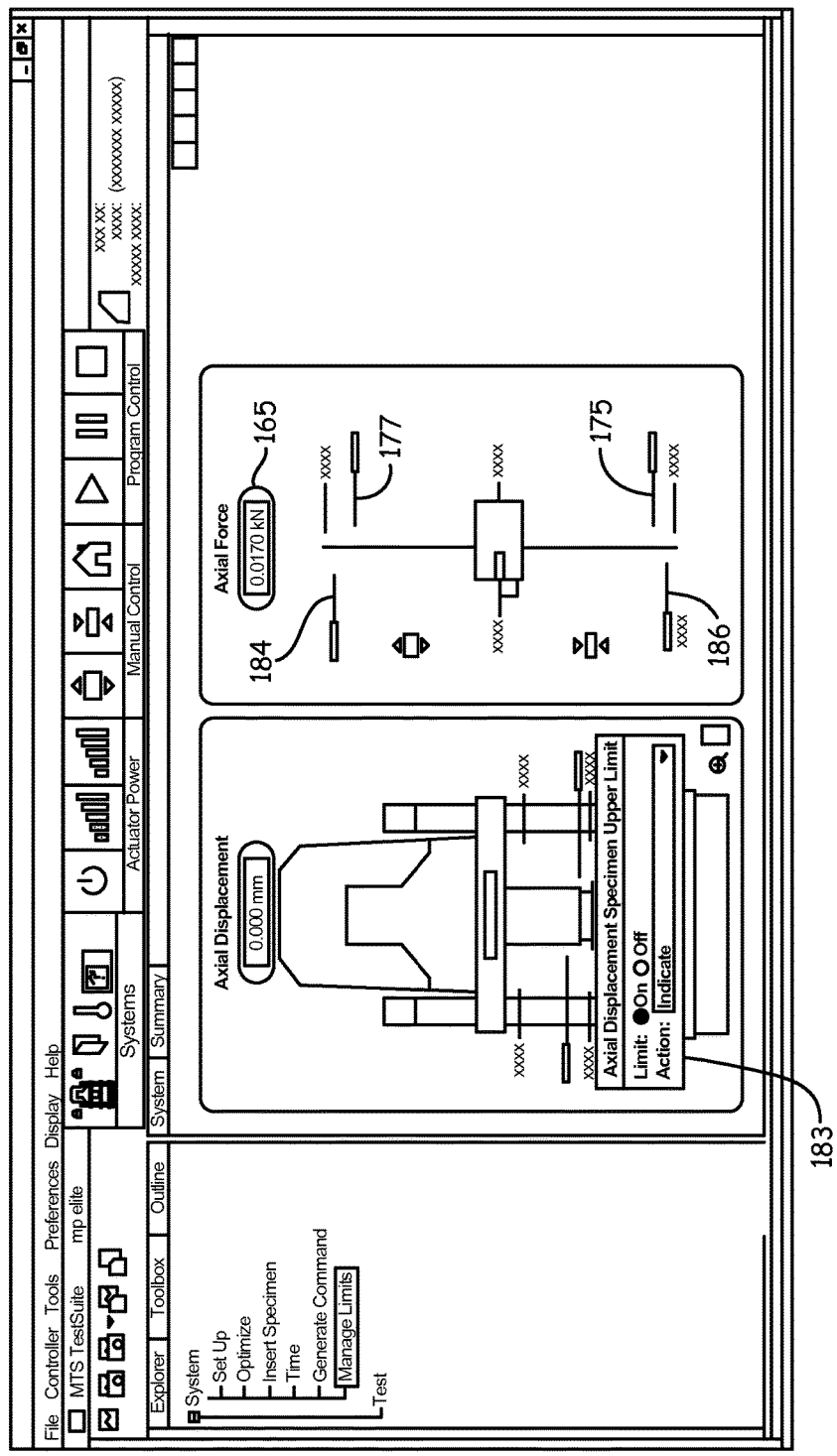

In addition to system limits of a parameter, such as system limits 180, 182 for actuator displacement, simulated visual representation of other limits can be provided by GUI 47 to define other ranges of the parameter the user wants to monitor. Although typically the simulated visual representation of limits comprise a pair indicating minimum and maximum values it should be understood that a limit may be one-sided and the simulated visual representation of such limits can include a single limit. For limits other than system limits, the user can turn the limit "on" (i.e., "activate", "enable") or turn the limit "off" (i.e., "deactivate", "disable"). In one embodiment as illustrated in FIG. 4, this can be accomplished by clicking on the simulated visual representation of the limit to be adjusted with a pointing device, or otherwise selecting the limit using GUI 47 and the simulated visual representation of the limit, and displaying and using a simulated visual representation of a button, slider, switch or the like, to turn the limit on or off. Based on whether the limit is turned on or off, the simulated visual representation of the limit can also change so as to indicate its operating status. For instance, a limit that is on can be of one simulated visual representation (e.g. certain color, shading or outline), while a limit that is turned off has a second simulated visual representation. Hence, by turning one of a set of limits off, a one-sided limit can be effectuated for the parameter and visually represented on GUI 47.

In one embodiment, limits are visually represented or manipulated on GUI 47 where the limits operate in a nested manner. In other words, each set of limits has operating values of the parameter being measured in smaller and smaller ranges. Referring to FIG. 3, a user may interact with GUI 47 to display a second set of limits that have operating values (maximum and minimum) that are each less than or equal to the corresponding operating values of system limits 180, 182. The GUI 47 advantageously renders this relationship. In one embodiment, this can be accomplished by clicking on the simulated visual representation of the limit to be adjusted with a pointing device, or otherwise selecting the limit using GUI 47 and the simulated visual representation of the limit, and changing the position of the simulated visual representation of the limit on the image 100 such as through a pointing device and moving it to a different location on the scale to which it pertains. However, if the user tries to change the position of the selected limit to a position corresponding to a value greater than the next greater range of limits, the GUI 47 will visually not let the user do this. In the case of a first set of limits having a range narrower than the system limits 180, 182, the user would be unable to visually move either of the limits that are nested within the system limits 180, 182 to locations on the scale 170 beyond that of the system limits 180, 182.

Any number of nested visually rendered limits can be provided on GUI 47 as desired by the user. If the user has three sets of nested limits being visually rendered, and if the user selects one of the innermost limits and adjusts its position visually on the scale 170, and if the desired position is beyond that of the next outer set of nested limits, the GUI can visually render that the next corresponding outer limit has been reached such as by a color change, blinking, etc. of the limit that has been encountered. If desired, GUI can also represent encountering of the next outer limit by visually moving that limit along with the limit that had been selected by the user.

By way of example, but advantageous for a testing machine having an actuator 15, three sets of nested limits can be visually represented on GUI 47. In addition to the system limits 180, 182 a next set of inner displacement limits can visually represent and correspond to a limit values corresponding to a fixture used with the test specimen. For example, the test specimen 18 can be disposed in an environmental chamber (which can also be visually represented on GUI 47) and where the second set of limits 185, 187 "fixture limits" having values defining a displacement operating range narrow than the system limits 180, 182 can correspond to the operating range of the actuator 15 so as not to cause damage to the environmental chamber such as incursion of grips holding the test specimen with upper and lower walls of the environmental chamber.

Figure 5:
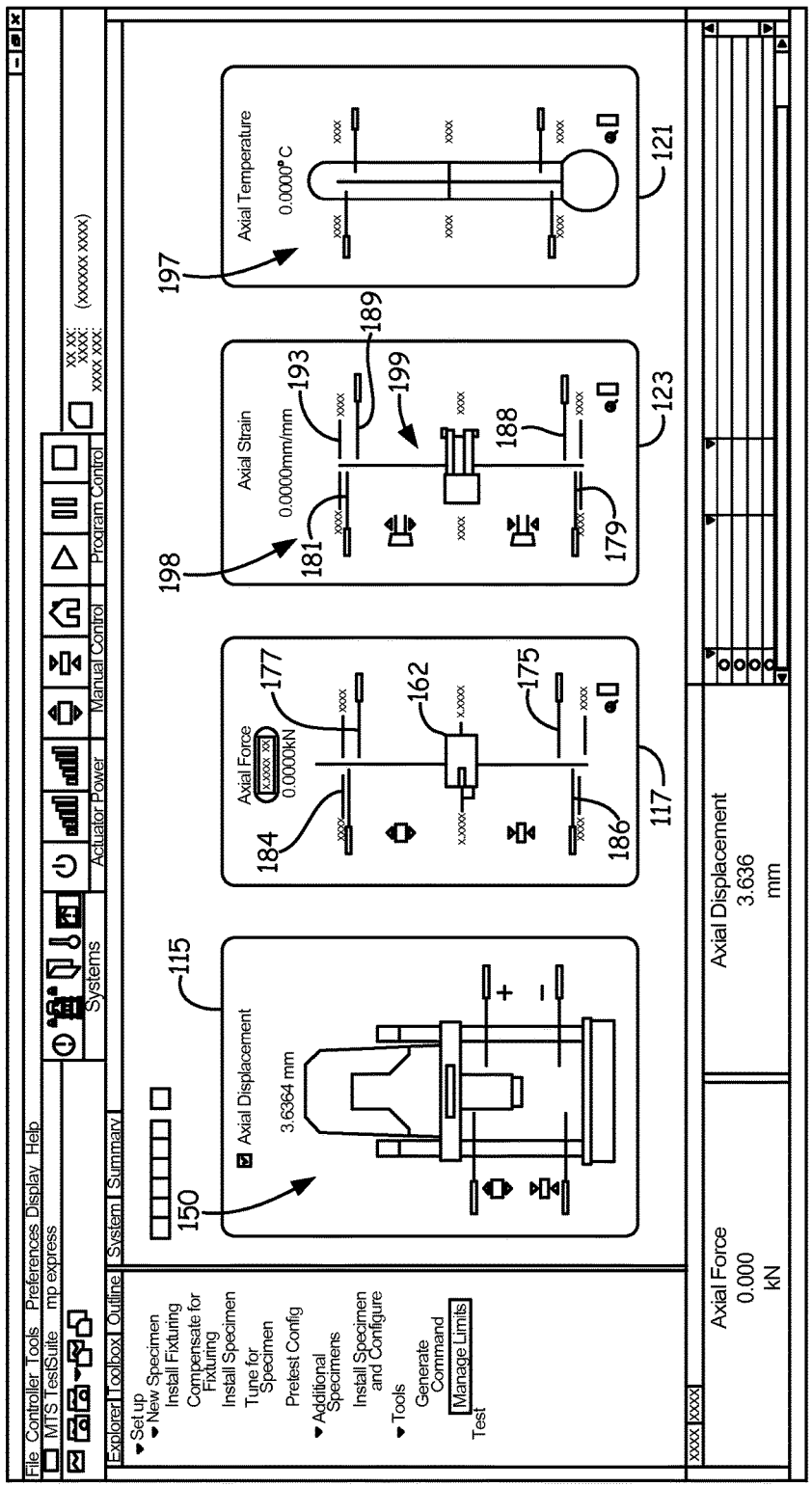

If desired a third set of nested limits 188, 189 can pertain to the operational limits of the monitored parameter for the test specimen "test specimen limits", such as the maximum amount of displacement or strain to be incurred upon the test specimen. This set of limits can be in addition to the second nested set of limits 185, 187 described above for the fixture (e.g. the environmental chamber), or in the alternative. In a manner similar to that described above, each of the limits of the nested set of limits can be turned on or off and, if desired, one or more actions to be undertaken by the testing machine 12, controller 14 or system controller 23 can be assigned. Although the test specimen limits 188, 189 can be displayed relative to system limits 180, 182, and fixture limits 185, 187, they can also, or in the alternative be displayed relative to an absolute scale 191 or relative scale 193 for strain of test specimen as illustrated in FIG. 5. Besides nested displacement limits as described above, nested limits for other parameters of a testing machine such as force in FIGS. 3-5, where load cell "system" or "component" limits are illustrated at 184, 186 and user configured test specimen limits for force are illustrated at 175, 177. Likewise, "system" or "component" limits of an extensometer are illustrated at 179, 181 in FIG. 5, where as stated above, test specimen limits for strain are illustrated at 188, 189 in FIG. 5.

It should be understood that limits pertaining to the relative scale 178 can also be visually represented and interacted with by the user using GUI 47 in a manner similar to that discussed above for the limits of absolute scale 170.

Another aspect of GUI 47 is that information related to a specific aspect of the testing machine is conveniently and accurately organized and rendered to the user. Referring to FIG. 3, information relevant to the aspect, "displacement," is grouped by visual border 115, while information relevant to the aspect, "force," is grouped by visual border 117. Generally, this information for each aspect can include but is not required or limited to visual rendering of the aspect, which can include the overall rendering of the aspect such as rendering of simulated visual representation 150, a "zoomed in" view of the aspect such as simulated visual representation 158 (each of which can include relevant visually rendered operating parameters, for example, displacement limits 180, 182, 185, etc.) and/or relevant controls for the aspect (e.g. dial 113). With the foregoing all being disposed within border 115 or border 117, the user knows the information being rendered is related to each other. Hence, if the user operates the dial 113 shown in FIG. 3, the user will know this will cause displacement of the actuator 15, either immediate displacement, or eventual displacement if configuring a test. If however, the user operated a similar dial rendered within border 117 (not shown in FIG. 3), force delivered (or to be delivered if configuring a test), will be changed accordingly. Stated another way, location of manual controls within border 115 or border 117 which defines an aspect or "Control Mode" of the testing machine (herein Control Modes include "displacement" or "force") intuitively conveys to the user what adjustment of the manual control will cause the testing machine to perform. Likewise, an aspect or Control Mode defined visually by another visual border could be related to temperature of an environmental chamber; hence the simulated visual representations will be related to temperature, the parameters visually rendered will be related to temperature and the controls will be related to adjusting the temperature. FIG. 5, illustrates a variety of other aspects or Control Modes of the testing machine that include "displacement" 115 (of the actuator), "force" 117 (of the actuator), "velocity" 119 (of the actuator or specimen), "temperature" 121 (of the environmental chamber or the specimen) or "strain" 123 (of the specimen). Clicking within the area of the screen bounded by a border causes a visual indication that the Control Mode has been selected, which can include but not limited to highlighting the corresponding border.

It should be noted that portion 104 can be larger than the physical area of the display screen that it is being rendered on. In FIG. 5, a plurality of different Control Modes are available for viewing. Clicking on and subsequent movement of scroll bar 201 allows portion 104 to be scrolled (in this example left to right and right to left) to see other Control Modes. In a further embodiment, the user can select and position each of the Control Modes within the portion 104 as desired. This can be very advantageous for it allows the user to easily see the changes occurring between each of Control Modes. For instance, if the test specimen under test is particular stiff, small changes in displacement (system) or strain (test specimen) will realize large changes in force applied to the test specimen. The GUI 47 allows the user to visualize and understand this relationship by simply positioning the Control Mode for force 117 proximate or adjacent to the Control Mode for system displacement 115 and/or Control Mode for test specimen strain 123. In addition, if desired, rendering of any of the Control Modes can be duplicated in portion 104. In FIG. 5, Control Mode 115 has been duplicated.

Figure 6:
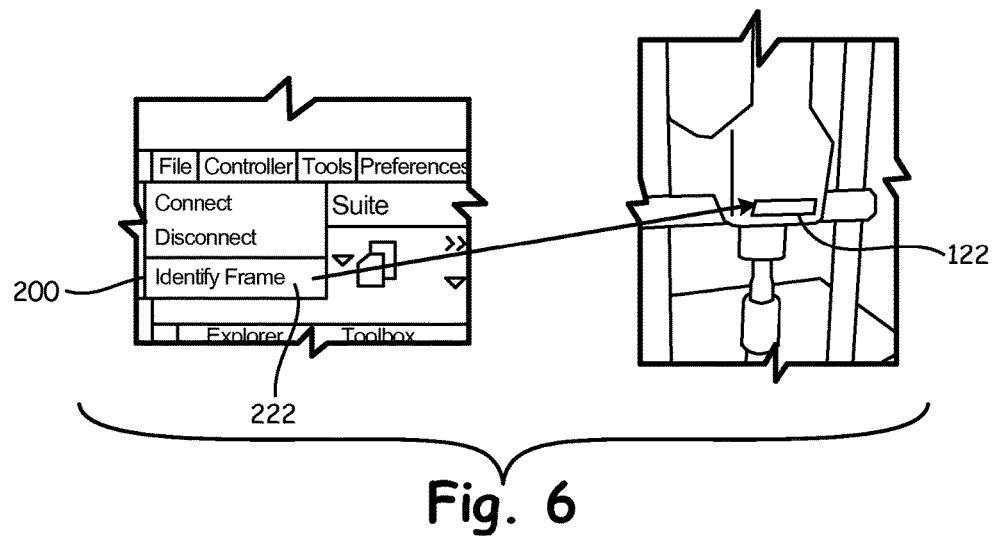

It should also be noted that GUI 47 is not limited to control and interaction with only one actual testing machine 12, but rather, GUI 47 is well suited to control and interact with a plurality of testing machines (even of different types) that may, for example, be in a testing laboratory. As discussed above, GUI 47 includes a simulated visual representation 150 of the testing machine 12. If, as in the embodiment described above, the simulated visual representation 150 is that of the actual testing machine 12, the GUI 47 thus provides the user with an easy way to identify which machine in the laboratory is currently being controlled or communicated with via GUI 47 simply by seeing the simulated visual representation 150 currently being shown in portion 104. If there exists more than two of the same type of testing machine in the laboratory to which the system controller 23 is connected with, additional visual indicators such as unique machine identifying text (e.g. "Machine A", "TEST STATION 1", etc. can be accessed and then displayed to the user by GUI 47, or can be continuously displayed to the user on image 100 such as at the top or proximate simulated visual representation 150 while the GUI is communicating with that testing machine. One convenient method for identifying the actual testing machine in the laboratory that the GUI 47 is communicating with includes activating the light 122 on the testing machine 12 to which GUI 47 is currently communicating with. FIG. 6, illustrates a specific embodiment of this method where the user accesses a command to identify the actual machine via a pull down menu 200 and clicking on "Indentify Frame" 222, at which time the light 122 for the machine under control of GUI 47 is activated. Activation can include but is not limited to simply turning it on, changing its color, blinking, etc.

Other simulated visual representations of other testing machines can be stored on the computing device 9, system controller 23 and/or controller 14 and accessed by GUI 47. In this manner, the user can have the accurate simulated visual representations of other types and models of testing machines to which the system controller 23 is selectively operably connected with. Each of the simulated visual representations can be associated with a digital file that also includes other information about that type of testing machine such as operating parameters, operating controls and functionality. In this manner, portion 102 can then render those icons, or even unique icons indicative of functionality that exists with the particular type of testing machine being controlled. Likewise, other parameters such as range of motion of the actuator rod of the actuator can be automatically known to GUI such that appropriate parameters, for example, system limits 180, 182 can be automatically incorporated into GUI 47.

In addition to having stored model specific parameters of testing machines that can be accessed and used by GUI 47, other components of the complete testing apparatus such as but not limited to the specific models of load cells, extensometers, environmental chambers, etc. can have stored parameter and functionality information that is accessible by GUI. These model specific components can be individually associated with the simulated visual representation 150 of the testing machine being displayed by GUI 47 such that representations thereof (e.g. representation of load cell 162) are accurate, but in addition, operating parameters associated with the individual component can be accessed and used by GUI 47 so as to accurately display as well as allow the user to accurately interact with component being rendered. For example only, the system limits of the load cell having visual representation 162 can then be known to GUI for display on image 100. With the system limits known to GUI 47 for the particular type of load cell, GUI 47 can then limit the user's adjustment of other limits (displayed as indicated above) to be less than those of the system limits. In other words, the test specimen limits 188, 189 could not be set beyond those of the component limits 185,187 of the load cell. In yet another embodiment, since the component limits 185,187 of the load cell are known from the stored parameters, the actuator force output of the testing machine can be limited so as not to damage the load cell. In a first situation, such as configuring a test or manual operation of the test machine, automatically knowing the component limits of the load cell and incorporating them into the operating parameters of the testing machine, then the testing machine will not let the actuator force be configured or manually adjusted to exceed the load cell limits. Likewise, if during a test, the testing machine is operating under displacement control where actuator force output varies depending on the amount of displacement desired, by automatically knowing the component limits of the load cell and incorporating them into the operating parameters of the testing machine, then the testing machine will not let the actuator force exceed the component limits of the load cell.

FIG. 5 illustrates a simulated visual representation for temperature at 197 and a simulated visual representation of an extensometer at 199 (which could comprise a photograph rather than a simulated visual representation since motion is not being simulated). Enabling GUI 47 to access stored information of operating parameters, operating controls and/or functionality of specific types of testing machines as well as other components such as but not limited to load cells, extensometers, environmental chambers, etc. and incorporate said operating parameters, operating controls and/or functionality into the functionality of GUI 47 including also rendering accurate visual representations thereof to the user, minimizes errors and saves time in both configuration and testing.

It should be noted that the visually rendered parameters are not limited to only "peak" values of a parameter such as peak loading or maximum or minimum displacement, but rather the visually rendered parameters can be based on any statistical function of the parameters such as but not limited to mean, peak-valley, average, etc. in any convenient domain such as time or frequency. Likewise, the limits can be set relative to the statistical function the parameter is being visually rendered as.

FIGS. 8 through 27 illustrate another aspect of the present invention. In general, the GUI 47 is constructed so as to guide or provide navigation for a user through proper setup of the test machine 12. Stated another way, the guided setup allows the user to navigate through information generated on the GUI 47 so as to set up the test machine 12 and optimize the system for his/her test needs. In particular, the GUI 47 will guide the user through the steps necessary to properly set up the machine, presenting controls needed or other information needed to complete a setup operation task or category of tasks. A significant benefit of this aspect is that the user does not have to remember the order in which to properly set up the machine, possibly failing to provide pertinent data. Instead, the user is continuously presented with information needed to complete system setup. As a result, the user is less likely to make any mistakes or otherwise set up the test machine 12 in an incorrect state. As explained further below in a preferred embodiment, selected portions of the GUI 47 retain the same purpose throughout set up thereby simplifying set up and reducing the need for the user to interpret the information presented as she/he does not have to remember where to go in order to determine generally where in the process they are, what information is being asked, the corresponding results, and modifications, if any, to the simulated visual representation 150.

Before continuing further, it should be understood that the set up procedure herein described is not limited to test machines for imparting tension and/or compression loads to a test specimen. Rather, aspects of the procedure can be applied to other actuator based test machines. Moreover, the specific order herein illustrated and described should not be considered limiting in that the order of at least some of the steps can be changed without departing from the benefits obtained from this aspect.

Figure 8:
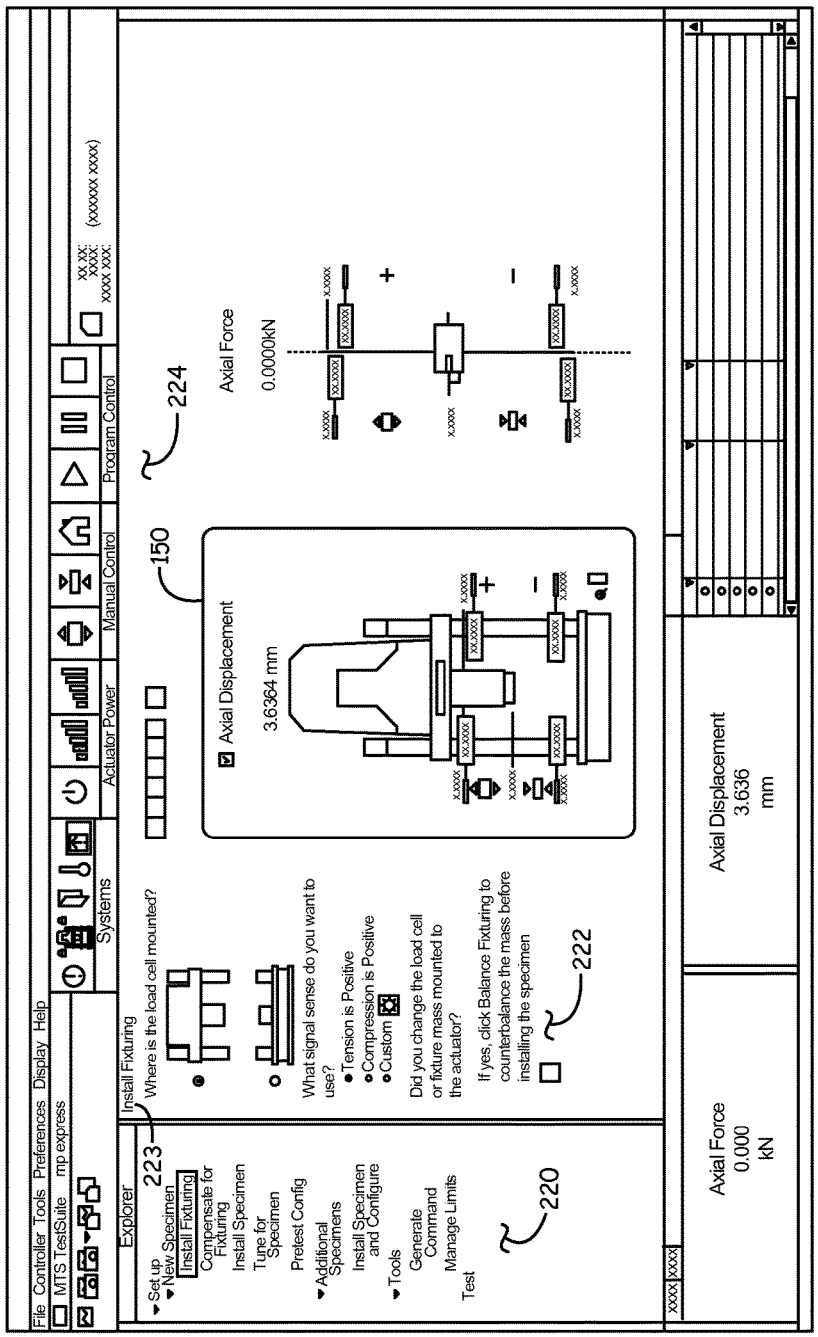
FIGS. 8-27 illustrate aspects for configuring a testing machine.

Referring to FIG. 8, the GUI 47 during the set up procedure can include three operating panels or portions, 220, 222 and 224. Generally, portion 220 (defined by a suitable border, if desired) provides the various steps involved during the set up procedure. In the exemplary embodiment, portion 220 is identified as "Explorer" so as to indicate to the user where generally the user is during the set up procedure, for example, by the highlighted text, which can function as operative links or buttons.

Portion 222, which can also be bounded by a border, if desired, is the portion of the GUI 47 to which the user will be asked for and or receive information related to the task highlighted in portion 220. An identifier 223 can correspond to the highlighted text in portion 220 to aid and/or reinforce understanding to the user. Advantageous questions and reports are discussed below. Portion 224 comprises one or more simulated visual representations (e.g. simulated visual representation 150) and provides "Situational Awareness" that may change based on the information and/or reports provided in portion 222.

In the illustrative embodiment, the general categories of tasks in portion 220 include "installing fixturing", "compensating for fixturing", "install specimen", "tune for specimen", and "pre-test configuration".

Figure 9:
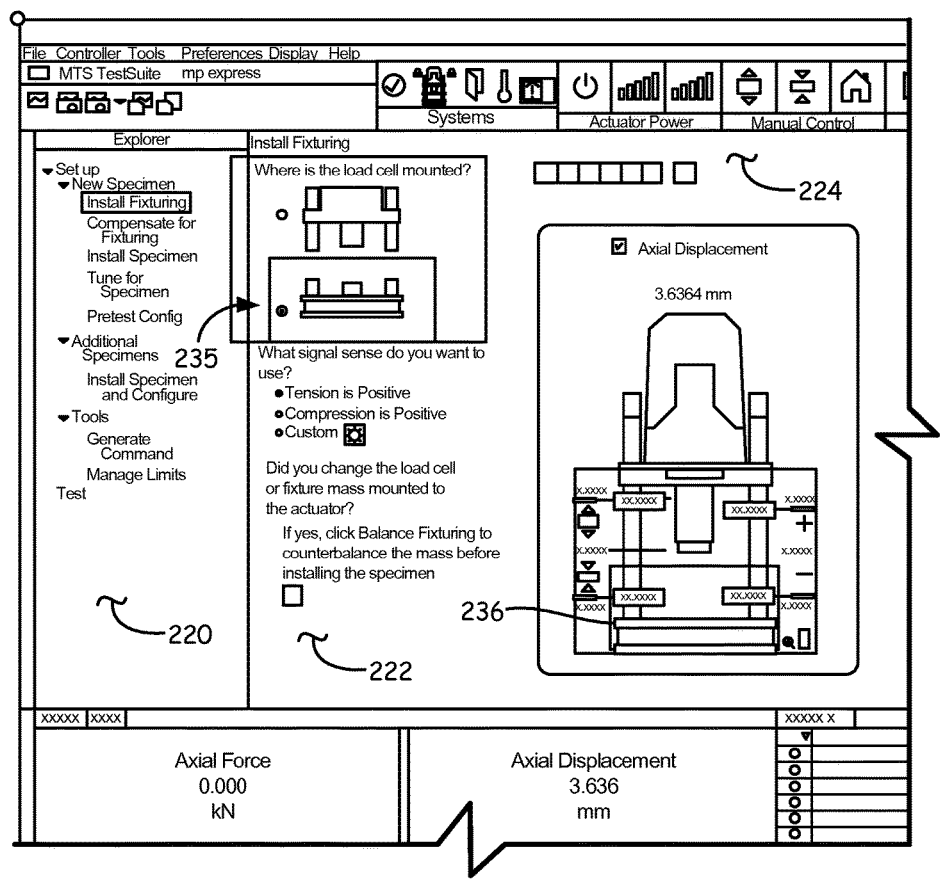

Referring now to FIG. 9, implementation of the procedure for installing the fixturing beings with activating one of two buttons 235. The question being specifically asked is where the load cell of the test machine 12 is to be located, either on the actuator 15 to move therewith or to a lower base platform. In an advantageous embodiment, upon selection of the location, the simulated visual representation 150 is updated as indicated at 236 in the example provided.

Figure 10:
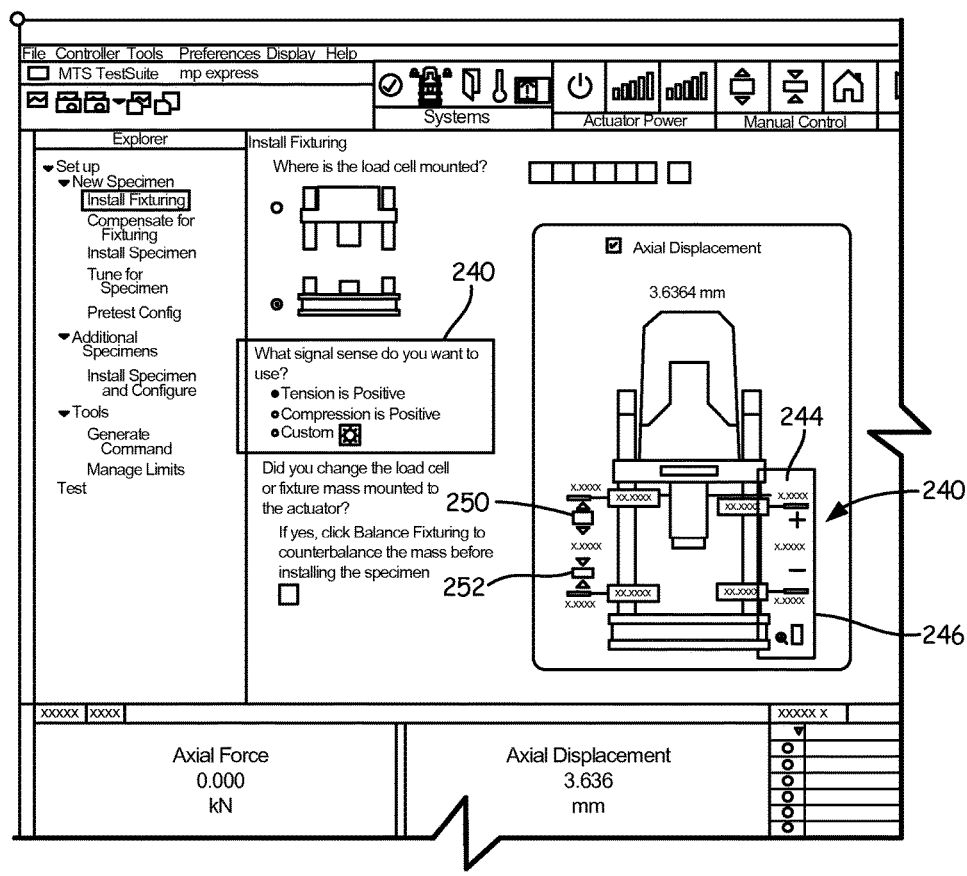

Next, as illustrated in FIG. 10, the user indicates at 240 which type of force will be considered positive for his/her application. This aspect is particularly useful since it allows the user to define a test in the manner most convenient for him/her without being restricted by the configuration or operation of the test machine 12, and in particular, the GUI 47 because it can be changed to meet the user's needs.

Setting signal polarity allows the user to specify which direction in the simulated visual representation 150 shows positive values and which shows negative values. Changing signal polarity is most commonly done when switching between a tension test and a compression test. Changing polarity does not change the actual (electrical) polarity of the sensor (e.g. load cell) or calibration; it simply changes how data is shown in portion 224. In addition, it can also control how data is shown in other places (scopes and meters), and how the test collects, stores and displays the data.

Depending upon the selection, there is visual indication on simulated visual representation 150. For example, when tension is positive, simulated visual representation 150 will have positive numbers 244 at the top of the diagram and negative numbers 246 at the bottom. Likewise, although not illustrated, when polarity is changed so that compression is positive, the minus and plus signs illustrated will "switch."

As a reminder to the user if the signal sense has been inverted, a minus and plus signs 248 appear on the right side of the simulated visual representation 150 in the Situational Awareness portion 224. It should be noted, when switching polarity, the location of specimen zero and the values and compression/tension symbols on the fixture side of the diagram remain unchanged.

Figure 11:
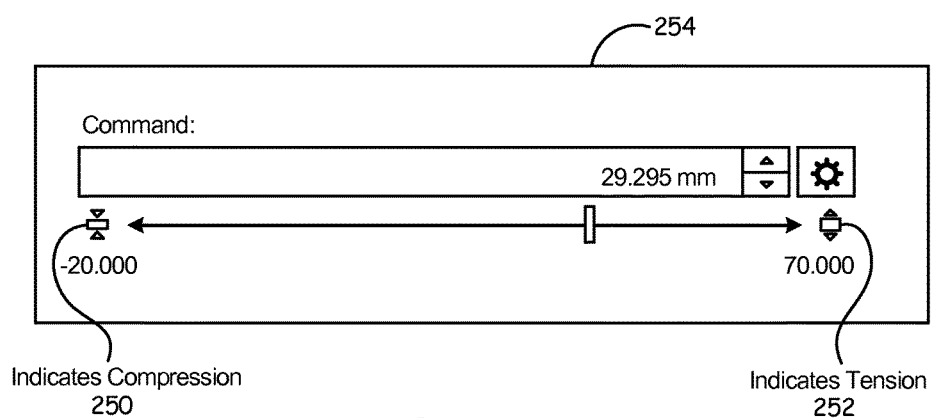

To further reinforce the selection of polarity and where tension and compression will reside in the test machine, icons 250 and 252 are provided to indicate tension and compression, respectively. These icons may be present in other portions of the GUI 47 where needed and to further improve understanding to the user of the nature of the control. In FIG. 11, an example is illustrated where manual control of the actuator 15, herein comprising a slider 254.

Figure 12:
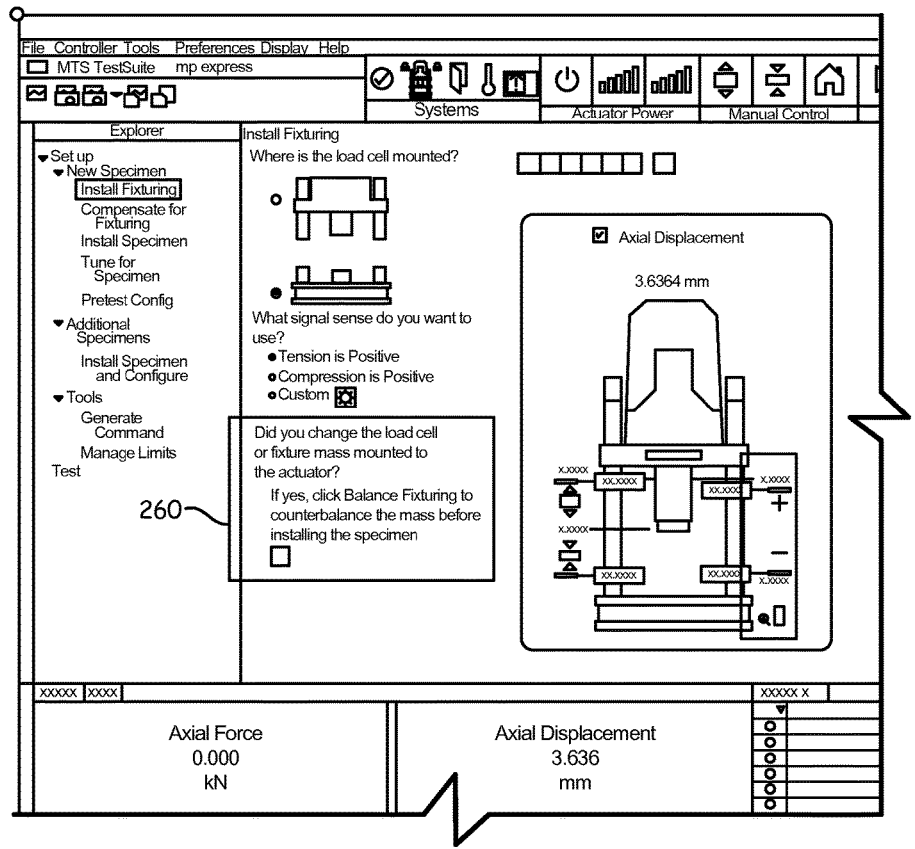

At this point it should be noted, the user may be required to perform or make physical changes to the test machine 12 as opposed to just working with the GUI 47. FIG. 12 illustrates an example of such a case. In the illustrative embodiment, the user was asked in FIG. 9 to indicate where the a fixture such as a load cell was to be located on the test machine 12.

The GUI 47 illustrated in FIG. 12 is an example of how the system can verify this physical act was performed correctly. In FIG. 12, the system performs a "Balance Fixturing" analysis, the information of which is indicated at 260. The Balance Fixturing analysis corrects for changes in the load cell and/or other fixture mass that may result in unwanted movement of the actuator 15. In particular, if the fixturing is mounted to the actuator 15, the actuator 15 will need to generate a force to hold the fixture in a fixed position. If the system is unbalanced, the unwanted actuator movement may occur when power is turned on or off. In general, balance fixturing is used whenever the fixture or load cell mass on the actuator 15 has changed, i.e. if fixturing is added to or removed from the actuator 15. This is an important step in test machine 12 setup and if not properly accounted for proper testing may not be realized.

The GUI 47 interface can visually indicate to the user if the test machine 12 is balanced and no action is required. On the other hand, if the test machine 12 is unbalanced, the GUI will communicate to the user, for example, in portion 222 or other noticeable indication elsewhere on the GUI 47 that fixturing needs to be balanced.

Figure 13:
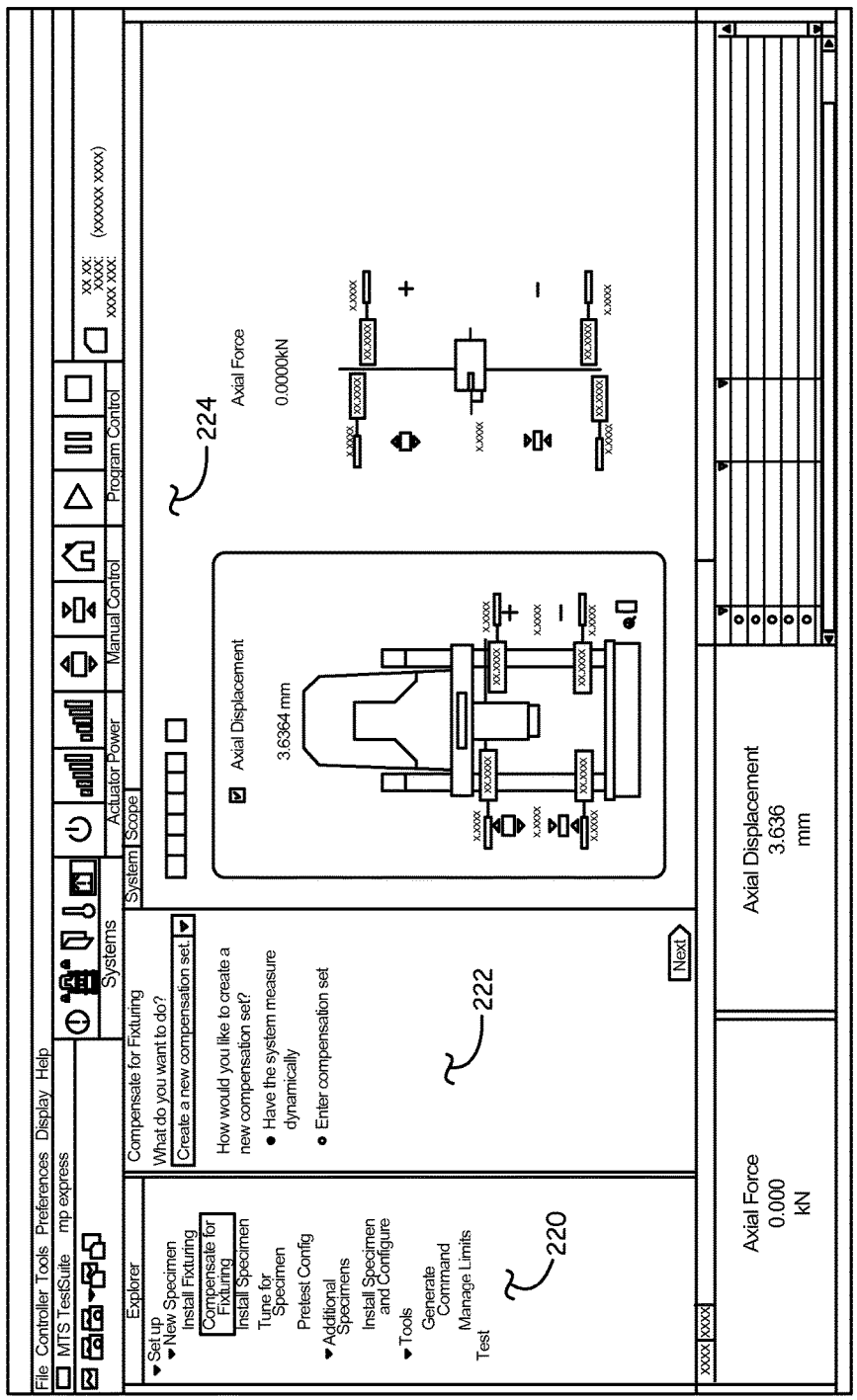

FIG. 13 illustrates progression of navigation in portion 220 to "Compensate for Fixturing" now reinforced in portion 222. Generally, a fixture attached to a force transducer (i.e. load cell) that is in motion, by being mounted to the actuator 15 causes unwanted feedback. This is due to motion in particular "acceleration" of the sensing bodies in the force transducer or load cell. Acceleration compensation is a technique that is often used in transducers such as force transducers. When such transducers are accelerated, this motion can cause error (inertial error) in the measurement. The transducer is comprised of a sensing element and additional mass attached to the sensing element. This additional mass can be fixturing mass or mass due to the structure of the transducer itself. Additional mass (not part of the unit under test) which is attached to what is known as the active side of the transducer will induce force onto the sensing element when the mass is accelerated. However, this inertial force is considered erroneous, because the force is not as a result of the force applied to the transducer from the unit under test but is instead a result of the force required to accelerate the mass of the fixturing and/or parts of the transducer itself.

For purposes of this application, the form or type of compensation that is provided to compensate for the above-described problem is not pertinent. One form of such compensation is described in co-pending application entitled "TRANSDUCER ACCELERATION COMPENSATION USING A DELAY TO MATCH PHASE CHARACTERISTICS", filed Mar. 14, 2013 and assigned Ser. No. 13/803, 773.

The particular feature herein described relates to guiding the user through this procedure at an appropriate time and providing GUI tools to easily enable the task to be performed, as well as providing to the user a measure of quality of the compensation that has been obtained, any and/or all of which further helps the user understand the purpose of the task, again providing the user a form of "situational awareness" for this type of testing.

Figure 14:
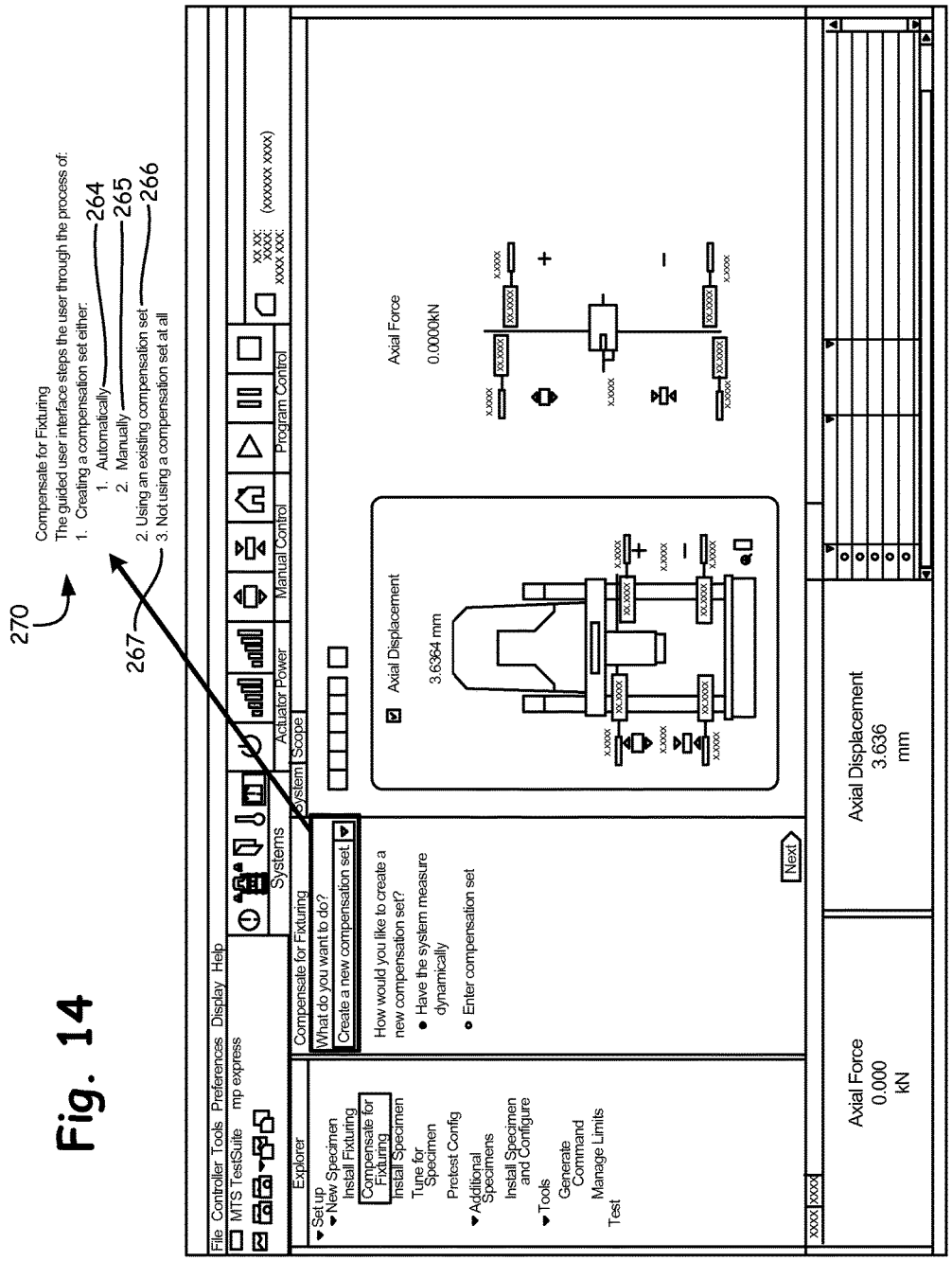
Figure 15:
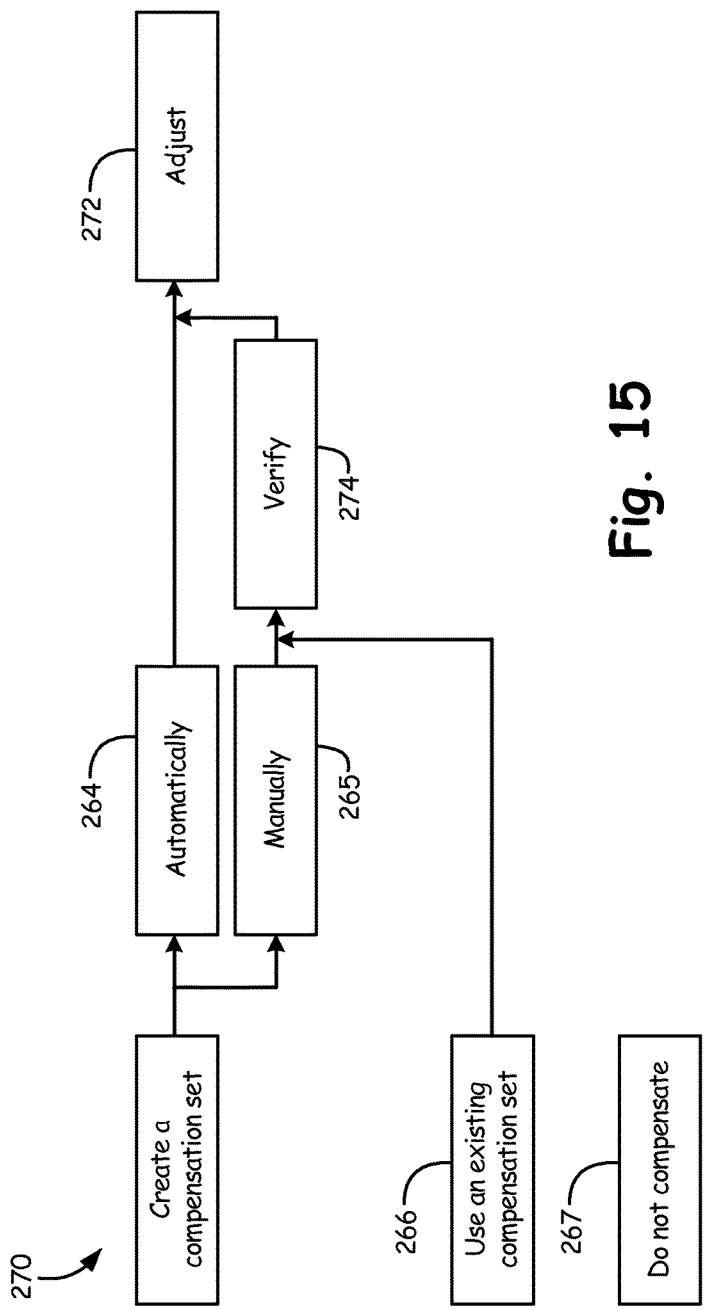

Referring to FIGS. 14 and 15, the user is presented with options to perform compensation, and if so whether to do so "automatically" 264 or "manually" 265; use an existing compensation set 266; or not to use a compensation set at all 267, collectively indicated at 270 in FIGS. 14 and 15. Irrespective of the knowledge level of the user, the user will at least be presented with the step, and depending on their knowledge/comfort level, the user can select which type of compensation to perform. A novice user may be likely or encouraged to allow the system to calculate a compensation set automatically, whereas a more skilled user may already know that a manual adjustment is what will be needed, or a previous compensation set can be used, or that given the test, compensation is not needed. The advantage again of the GUI 47 and the guided navigation is that each of these users will be presented with the task such that the step is not overlooked when in fact compensation is needed.

If the user desired a compensation set to be automatically ascertained at 264, the user can further attempt to adjust the set at 272, if desired, and as explained below. Such adjustments could include one, some or all of that available under manual adjustment 265, after which the GUI 47 will report or "verify" the results of the compensation obtained at 274. Depending on the results obtained, the user may return to the automatic calculation at 264, or continue to try other adjustments 272, which can include verifications. In a similar fashion, if the user instead chose to manually try to provide compensation at 265, steps of verification at 274, and if desired, further adjustments at 272. Upon achieving desired results or no further improvement as described below, the user at can choose to continue to the next step.

Figure 16:
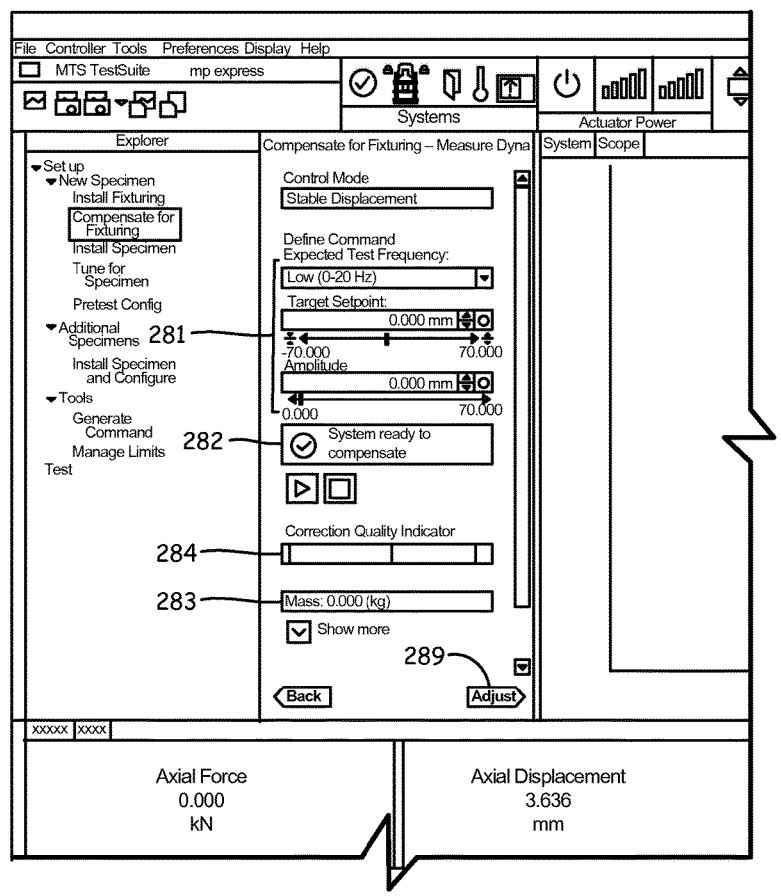

FIG. 16 illustrates guidance of the user through "automatic" compensation for fixturing. In general, the automatic process determines appropriate values for mass compensation, while the GUI 47 indicates whether or not the system is ready to compensate.

In the automatic process, the user enters command values indicated at 281 for the random (noise) movement of the actuator 15 and runs the command at 282. (A graphical representation of the movement of the actuator 15, and if desired, the output of the transducer can be displayed in portion 279.) The system will return a measure of correction quality as indicated at 284 and returns the values indicated in 283.

The indication of quality 284 can take any number of forms such as various scales, percentages, broad indications of "poor", "good", "excellent" and the like. In the embodiment illustrated, a particularly advantageous indicator is that of a "colored" indicator having two or more colors. For example, a good indication of the quality of compensation may be located at the right end and in "green", while the opposite end where compensation is low, a color of "red" is provided. A "yellow" area between the "red" and "green" can be provide in the center, indicating that some compensation may exist but it may not be sufficient. It should be noted though that depending on the test specimen, achieving an indication of "good," "excellent," or "green" quality level may also not be achievable.

The GUI 47 presents to the user relevant parameters for the test and/or evaluation, such as but not limited to, the range of frequencies for the test, the limits of displacement and/or force that the test will employ. These parameters have been found to be particularly pertinent for tension and/or compression testing, although other parameters could be customized or otherwise presented given more information from the user as to the type of test being conducted, including the type of material generally, length of the specimen, mass, etc. on the test machine 12 herein illustrated or on other forms of test machines.

Upon entry of the parameters indicated at 281, the user can activate the "play" button 288, at which time the test machine 12 will operate. After completion, the GUI will provide an indication of the mass of the fixturing, specimen and other elements attached to the load cell 20A, which in turn, is attached to the actuator 15.

As indicated above, the GUI will also provide a measure of quality of the compensation 284 ascertained. Historically, such an indication has not been provided, thereby leaving the user with little guidance as to whether the compensation obtained is good, bad or fine. Without sufficient experience, and even with experience, but maybe not on the current test being employed, the user makes a subjective decision on whether the compensation is appropriate. The GUI 47 herein provides the user an indication; hence, a measure of objectiveness that the user can proceed as well as possibly providing feedback that the user can use to gain intuition.

In some prior art techniques, compensation is ascertained by making adjustments as the actuator is oscillating, and if the sensor output indicates also a varying signal, compensation is not good because although the fixturing is moving, it is desired that the output signal from the sensor be zero (because during such initial testing no specimen is attached). In the prior art systems, the user can move a slider, turn a knob or the like until the sine wave of the sensor output has reduced to an acceptable level. The difficulty for the user however is when is it good enough given the parameters of the test. The system herein includes historical data, algorithm or the like that can be accessed (internally or remotely if connected to a wide area network, if desired) and presented to the user based on the test parameters and the output from the sensor during the test to indicate to the user whether the compensation achieved may be appropriate. In particular, for a less experienced user such information is particularly valuable in order to have confidence in the test results obtained after proper configuration.

If adjustments are desired after receipt of the compensation results, the user can activate the "adjust" button to make some adjustments as stated above with respect to FIG. 15 at 272.

Figure 17:
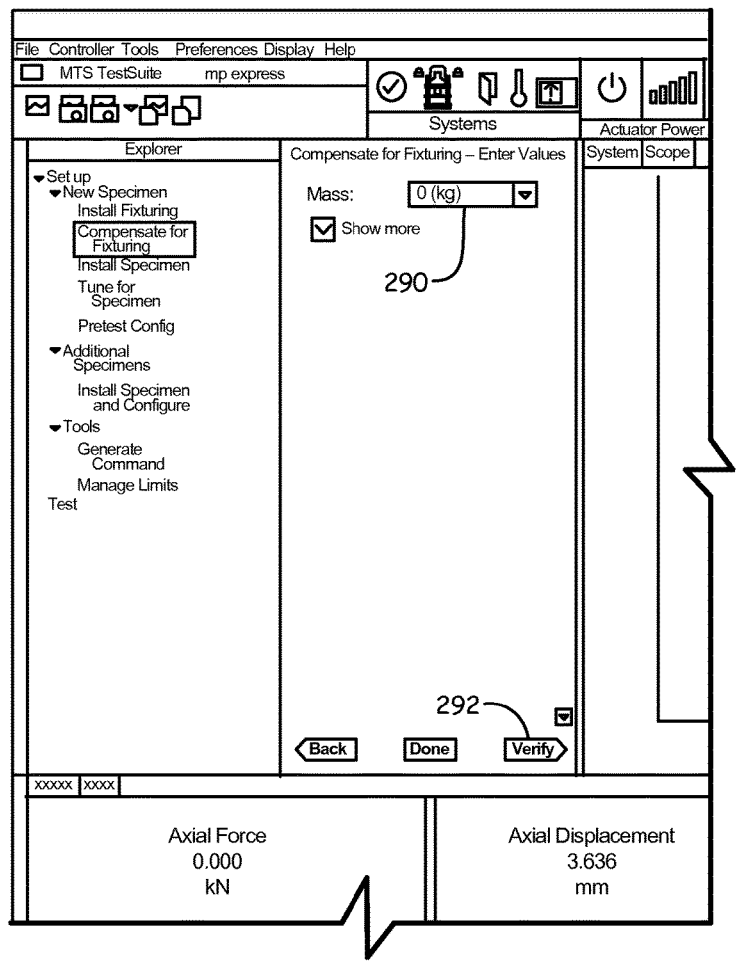
Figure 18:
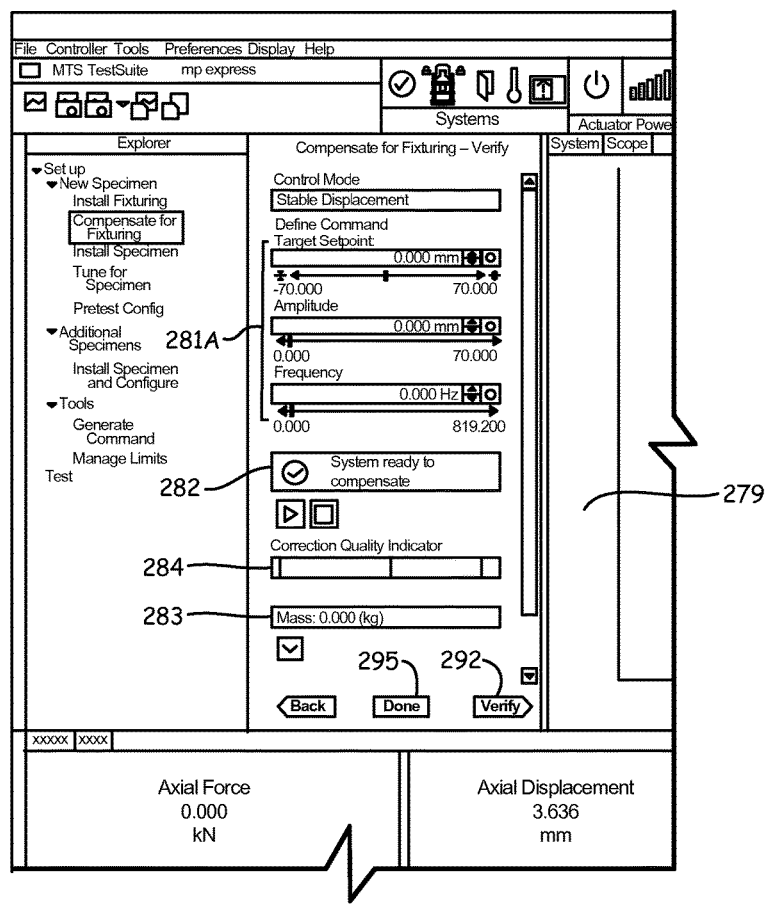

FIG. 17 illustrates an exemplary manual entry of data, herein where the user enters the believed mass of the fixturing at 290, for example, 1 kg. which is illustrated as entered at 283 in FIG. 18. It should be noted the defined command of the oscillatory movement in FIG. 18 is that of noise rather than that indicated in FIG. 16.

Figure 19:
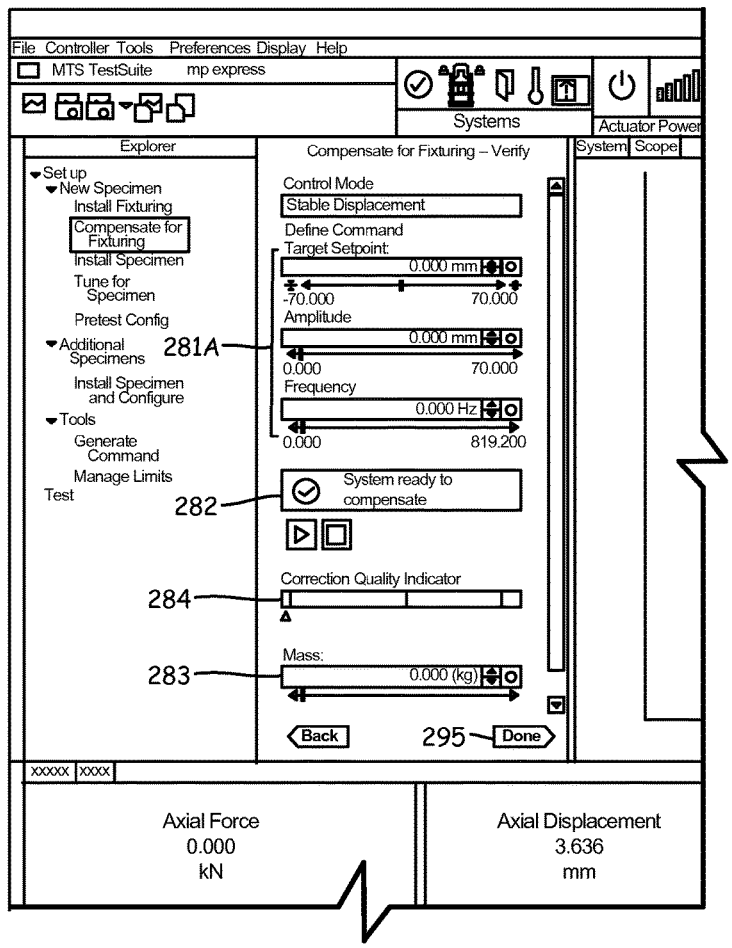

If after the verifying results of FIG. 18 have been presented, the user can activate button 292 "adjust" upon which the user is presented with a GUI as illustrated in FIG. 19 whereat the mass can be adjusted and tested using the parameters 281A indicative of sinusoidal waveform rather than noise as indicated at 281 in FIG. 16. Upon achieving a suitable indicator of compensation, the user can activate button 295 to exit the "Compensation for Fixturing" category of tasks.

Figure 20:
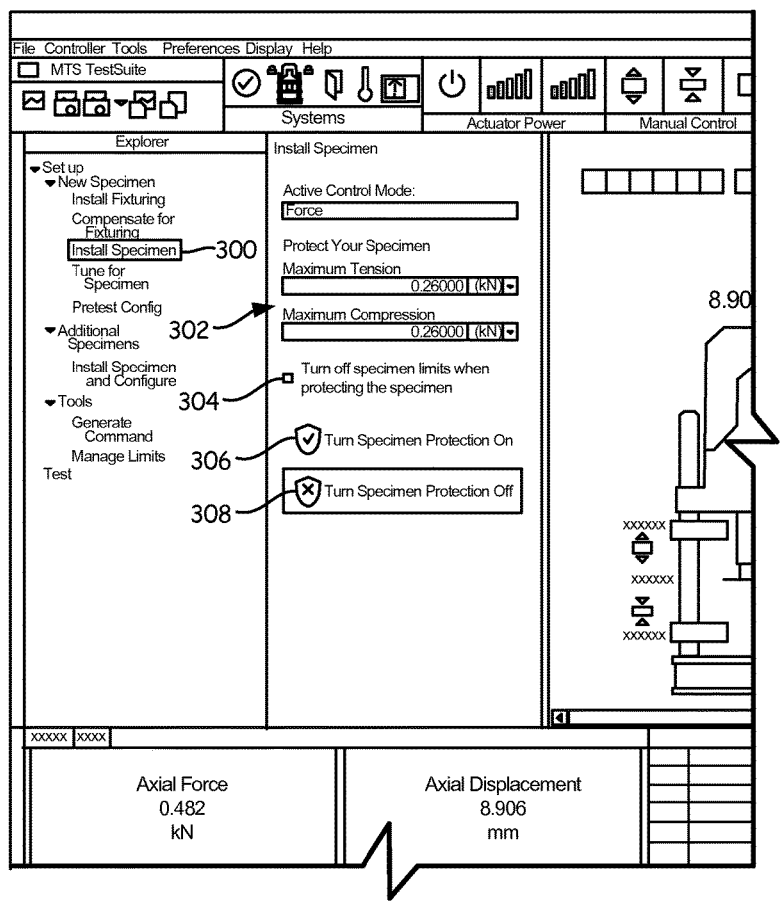

FIG. 20 illustrates the next category of task that being "Install Specimen" as highlighted in portion 220 at 300. As with the other general categories of set up described above in order to provide a consistent presentation to the user, portion 222 is again used to present to the user questions and information pertaining to the task of Install Specimen. As illustrated, the user can use "Install Specimen" to protect the test specimen during the installation procedure. In particular, the user can enter values for maximum forces 302 (tension and compression) to be applied by the actuator 15. At this location, the user indicates the maximum forces he/she wants the actuator 15 to apply during testing. In other words, the clamped the capabilities of the actuator 15 during testing. It should be noted the forces indicated are not the measured forces, but rather the amount generated by the actuator 15 based on, for example, limiting hydraulic/pneumatic pressure provided to the actuator 15, or limiting current provided to the actuator 15, if it is an electric actuator.

If desired, specimen limits can be turned off at 304 so they are not inadvertently triggered while installing the specimen in the specimen protection mode 306. When specimen protection mode is turned on 306, a Stable Displacement control mode becomes active. Specimen protection can be turned off at 308.

Figure 21:
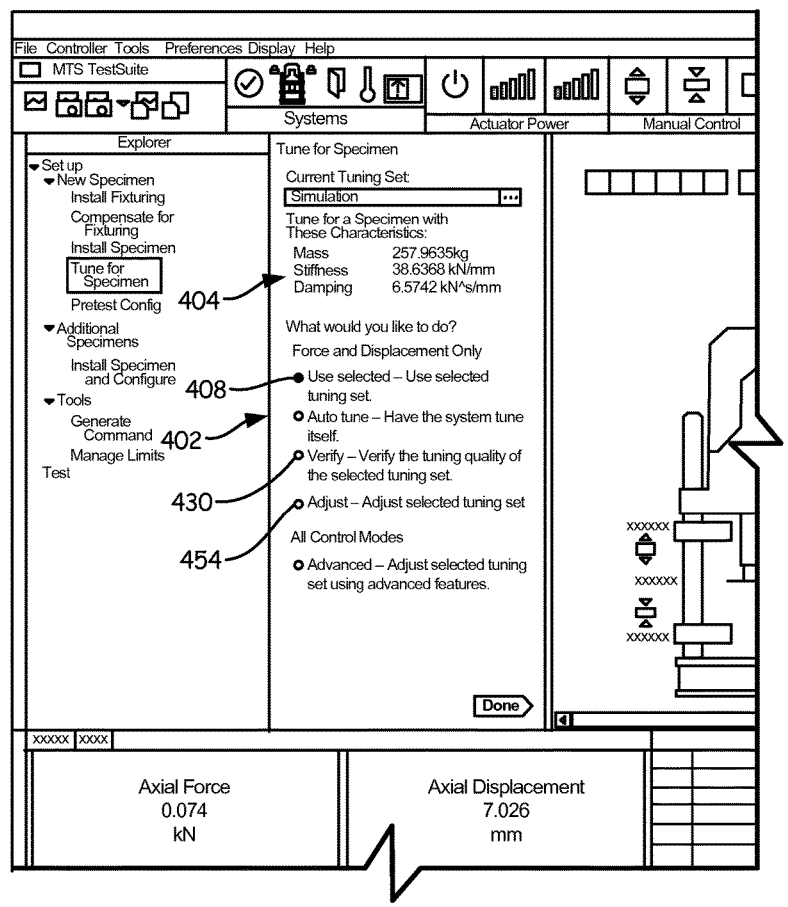

FIG. 21 illustrates the next category of tasks that being "Tune for Specimen" as highlighted in portion 220 at 400. Recapping what has already occurred, the user has defined the test machine, indicating among other parameters the location of the fixturing and the polarity of the test results. With the fixturing mounted in the test machine 12, compensation for the fixturing has been ascertained. The specimen was then installed as indicated above with some operational limits defined, if necessary and as desired.

With the test specimen now mounted in the test machine 12, the control parameters for the test machine 12 based on the test specimen being tested need to be properly ascertained. For instance, the control parameters for testing a stretchable band would be different than testing a stiff metal specimen.

Traditionally, this step has involved specific adjustment of the control parameters such as gains in, for example, and without limitation a (PID) controller. Although there exists techniques for automatically providing such tuning (in a manner generally similar to that discussed above with Compensation for Fixturing), the specific techniques are not pertinent to the aspects herein described. Rather, this aspect of the invention pertains to the GUI 47 for guiding the user through this process having already guided them to a test machine 12 configuration where such tuning is now appropriate. The GUI 47 is particularly helpful because the process of test machine 12 configuration is guided and consistent for a test engineer or operator of all skill levels.

Figure 22:
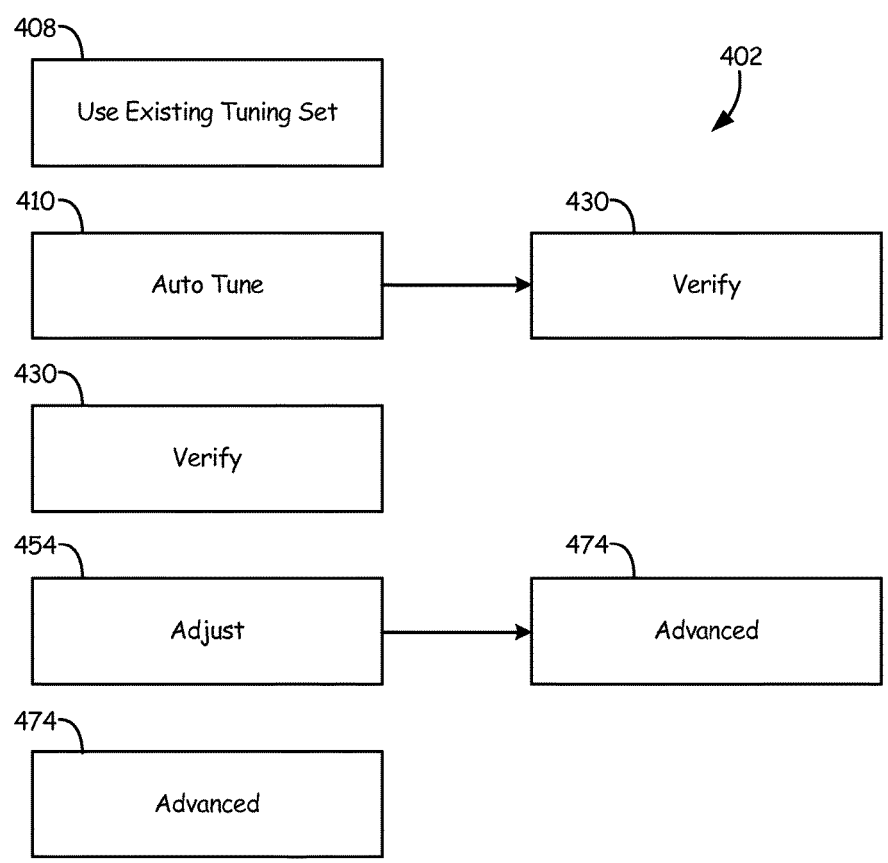

Referring to FIGS. 21 and 22, user selectable options regarding tuning are indicated at 402 in portion 222. Of particular note in FIG. 21, is that the GUI 47 displays all the specimen parameters at 404 (mass, stiffness and damping). (In FIG. 21, specimen values 404 are the previously ascertained set.) A first selection the user has as illustrated in FIGS. 21 and 22 is to use a previous set of values.

Figure 23:
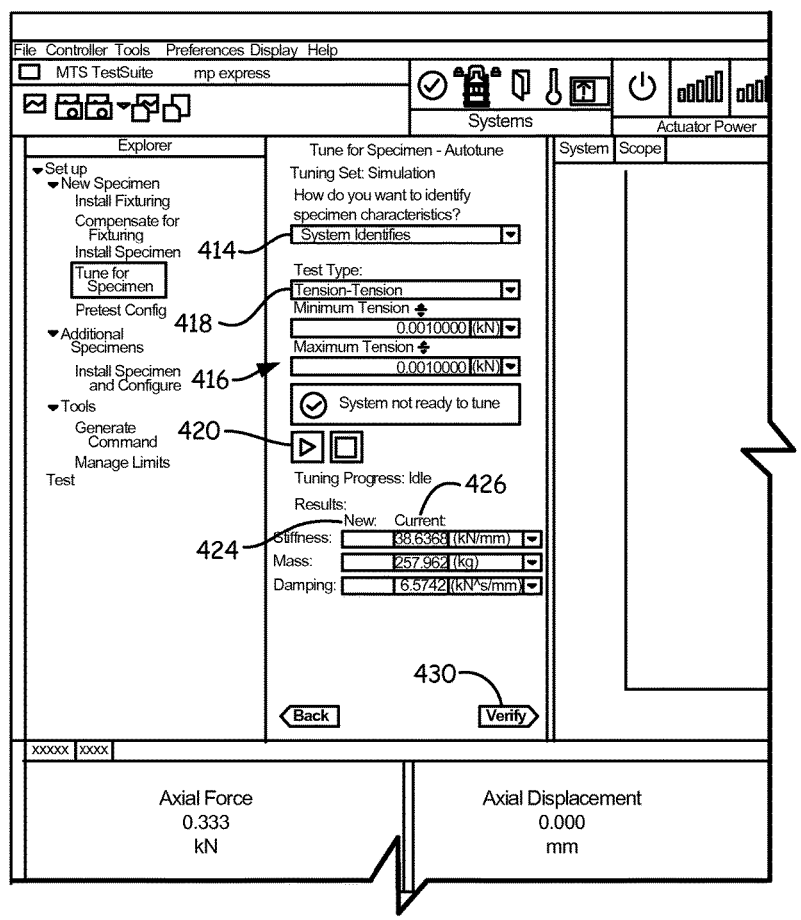

If desired, the user can select "Auto Tune" 410. Referring to FIG. 23, there are two ways that the test specimen characteristics 404 are derived for tuning. The user can enter them or the system will identify them. At 414, the user can identify the type of command to apply to the test specimen. At 416, in addition, the user enters the minimum and maximum force values to apply to the test specimen when for a type test provided at 418. It should be noted, the parameters indicated at 416 are determined based on the selection at 418. Commonly, this has been a problem for users; however, by encoding the possible parameters as a function of the input provided at 418, errors during tuning including specimen damage are reduced. Typical selections for input 418 include (tension-tension; tension-compression; and compression-compression).

The system generates the modeling program specified at 418 to determine the specimen's characteristics 404. After activating a play icon 420, the tuning procedure is executed with resultant ("new") specimen characteristics provided at 424 compared to the "current" values indicated at 426. Commonly, the actuator 15 movement is a noise profile (random, or selected).

If the specimen values appear appropriate, the user could selected the button "done" (although not highlighted); however, to explain further aspects, the user can select the button "verify" 430.

Figure 24:
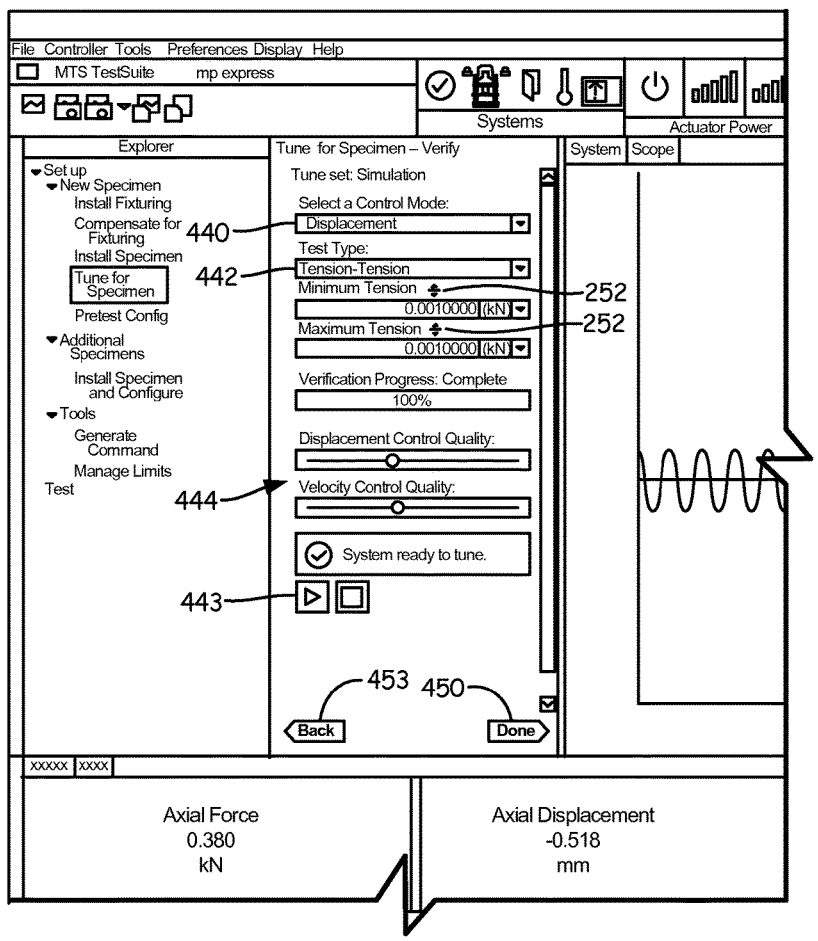

FIG. 24 illustrates the verify step obtained by activation of the "verify" button 430. As with the Compensation of Fixturing discussed above, GUI 47 as illustrated in FIG. 24 includes indicators to remove the subjectiveness previously present in test machine systems during tuning in order to give the user an indicator of quality or correctness of the values obtained.

Generally, the Verify step illustrated in FIG. 24 allows the user to verify the quality of the tuning set obtained. In particular, the user selects a control mode at 440 such as displacement or force. The type of test to apply (or being applied) is provided at 442. It should be noted the icons 250, 252 are displayed as a function of the test to apply to emphasize to the user the test being applied. The user can again enter the minimum and maximum force values as appropriate.

Upon completion of the verify execution as indicated at 442, quality indications 444 are rendered in any number of suitable formats using absolute/relative scaled numbers, percentages and the like. Herein the indicators comprise colored sliders that indicate quality of the tuning values obtained for the selected control mode. The indicators 444 illustrated are particularly useful in indicating whether the system is over-tuned ("hot"), where the indicator (slide button) is to the right, while an under-tuned system is sluggish, and the indicator (slide button) will be positioned to the left.

The indicators illustrated are particularly advantageous for using a pointing device such as a mouse; however, the indicators again should not be considered limiting. Using the indicators 444, the user can attempt to adjust the tuning values in order to change the responsiveness of the system by then activating a play button 443, at which point the verify step will be re-executed to see if improvement was made in the direction desired by the user sliding the indicators. For example, new indication(s) such as Displacement Control Quality would then be obtained. The indications of quality are based in part on control theory. If the quality values indicated are appropriate, the button "done" 450 can be activated.

If however, the indications of quality are not satisfactory, or the user desires to try to improve the quality of tuning, the user activates the "back" button 453 and the GUI 47 returns, in the illustrated embodiment, to FIG. 21. At the GUI illustrated in FIG. 21, the user can select "Adjust" at 454, at which point the GUI 47 renders the image of FIG. 25. The user can go back and adjust; however, the user can also do an adjustment using the quality indicator slider in order to improve results.

Figure 25:
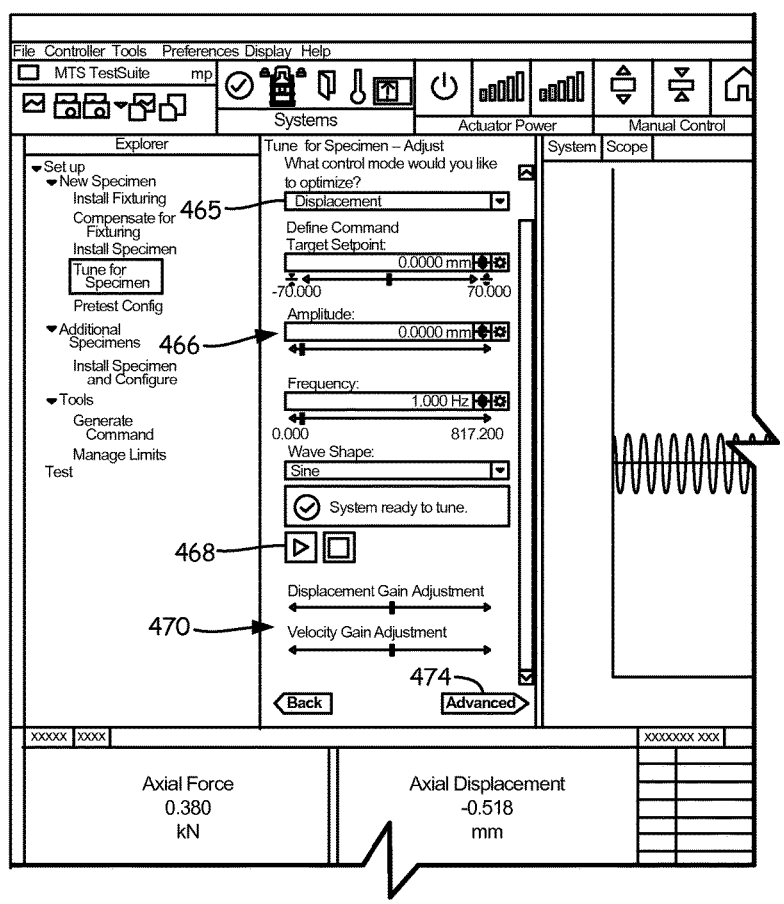

In FIG. 25, the user can adjust master tuning controls while applying command and observing system response. In particular, the user can select a control mode at 465; define a program command appropriate for anticipated test values at 466; run the tuning program by activating button 468, after which the user will observe the system response and adjust individual gains at 470. The adjustments indicated at 470 comprising displacement and velocity, although only two in quantity, can affect numerous control parameters (such as 17 different control parameters, depending on the controller construct being implemented); hence the GUI 47 of FIG. 25 is particularly advantageous. Nevertheless, the GUI 47 is also advantageous by allowing different levels of adjustment from just a few adjustments (e.g. indicators 444 and/or 470) to numerous values available on an image not shown but reachable through button 474, the complexity and difficulty, and hence skill level needed makes such adjustments difficult to master.

Figure 26:
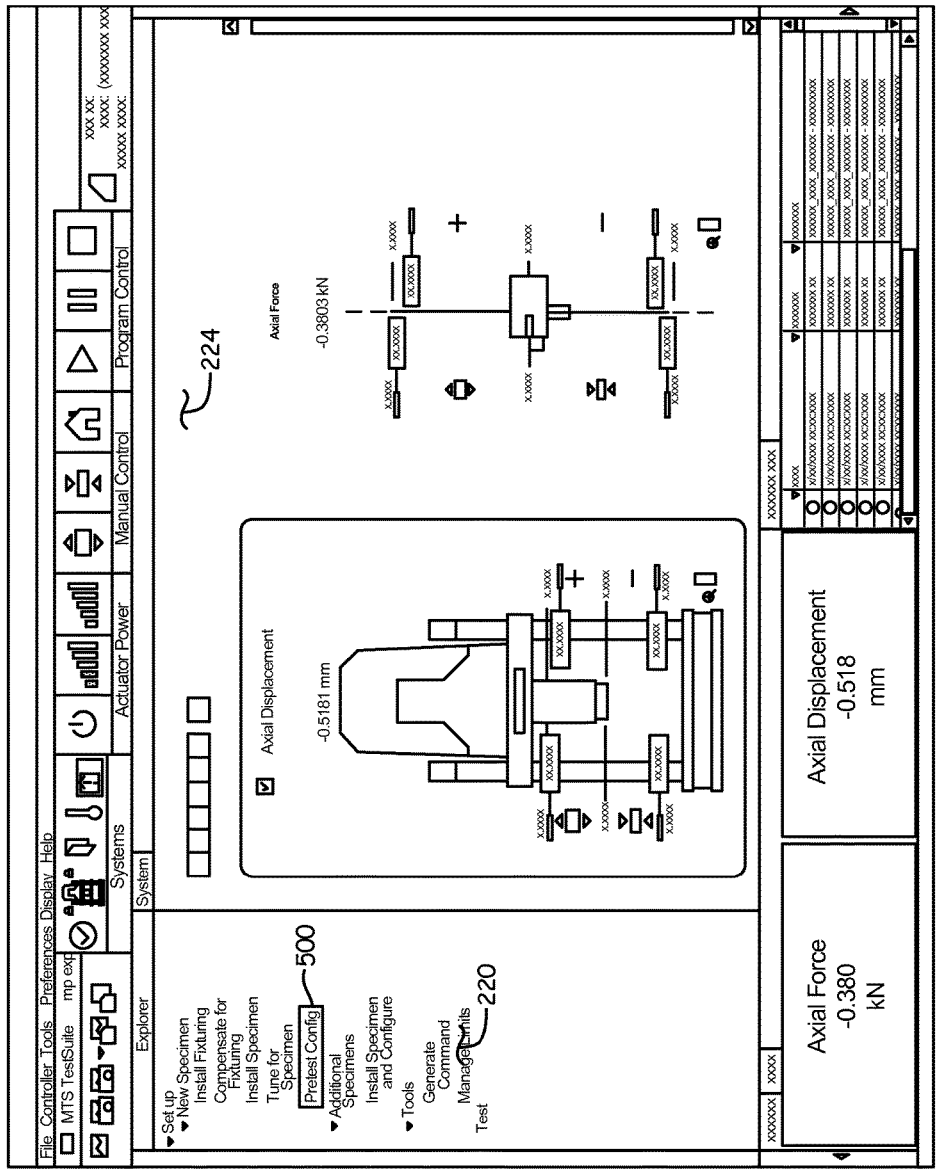

FIG. 26 illustrates the next category tasks of "Pretest Configuration" as highlighted in portion 220 at 500. In this category, the user is near or ready to start testing. With this GUI, the user can use manual command buttons to move the actuator 15 to a starting position, where the simulated visual representation 150 tracks movements of the test machine 21. In addition, the user can go back and adjust, however, the user can also do an adjustment using the quality indicator slider in order to improve results.

Figure 27:
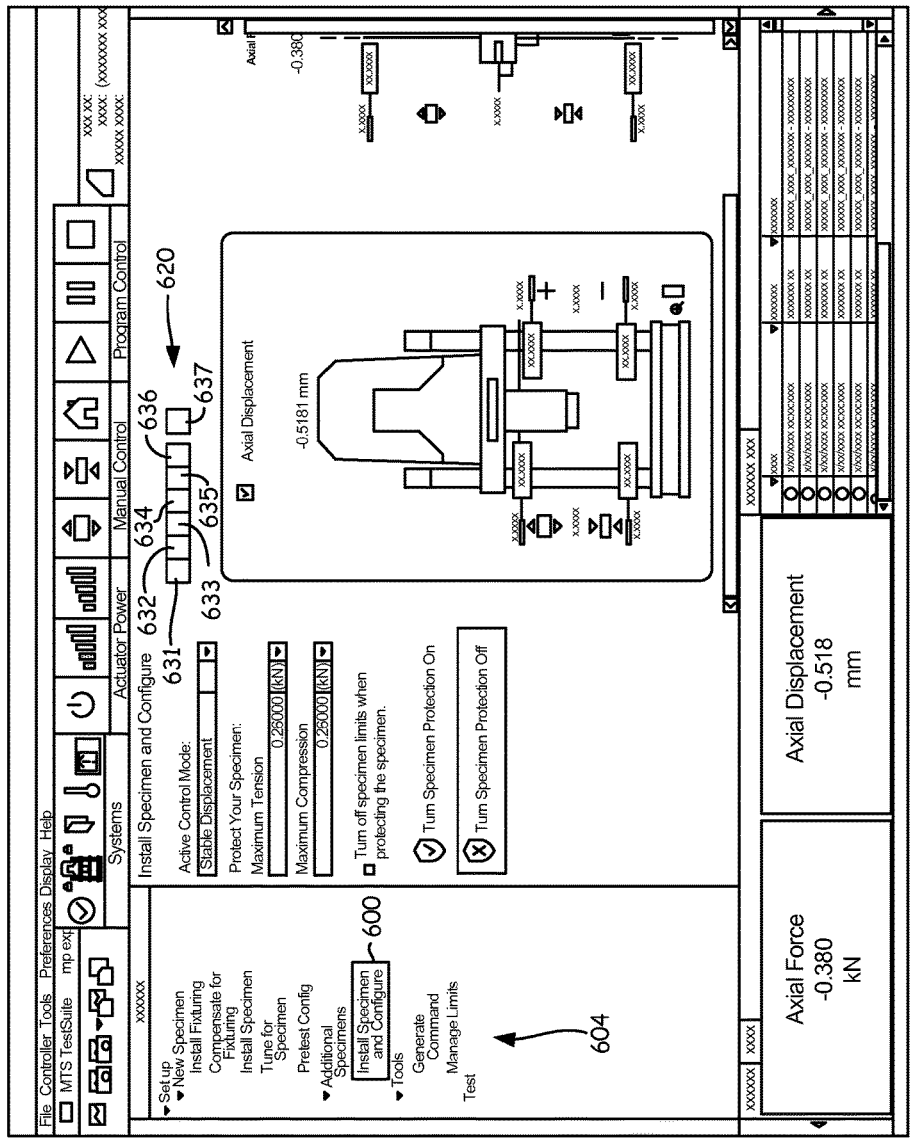

FIG. 27 illustrates a next category tasks of "Additional Specimens" "Install and Configure" as highlighted in portion 220 at 600. This GUI allows the user to easily use the same configuration for similar specimens in a series of specimens to be tested. As appreciated by users, the GUI(s) are organized in the manner to accomplish testing in an efficient manner for any number of specimens, allowing reconfigurations as needed, but insuring such reconfigurations are complete.

FIG. 27 also illustrates a category of "Tools" 604, which are not part of the workflow necessary to configure the test machine 12, but are those tools that would be commonly used by the user and thus placement in the portion 220 allows ready and convenient access. The last category relates to setting up specific "Test" 606 whereat GUI interfaces can be provided to specify the types of tests that the test machine 12 will apply, but not pertinent to the invention herein described.

FIG. 27 like many of the other Figs. illustrate that the portion 224 can include a Layer Control Panel 620. The layer control panel 620 comprises a series of buttons allowing the user to visualize the logical architecture of the testing system. As illustrated, the layer control panel 620 can include "toggle" buttons which when selected add or remove a "layer" from the simulated visual representation 150 to allow the user to display what is most important or selectively review settings made. In the embodiment illustrated, button 631 is for Fixture Limit sliders; 632 is or Specimen Limit sliders; Fixture and specimen limit values 633; 634 is for Offset references; and 635 is for peak and valley indications; and 636 is for user Help information. Button 637 allows the user to add/remove or reorder signal views or customize the order in which the signal views are shown in portion 224.

Although the subject matter has been described in language specific to structural features and/or methodological acts, it is to be understood that the subject matter defined in the appended claims is not necessarily limited to the specific features or acts described above as has been held by the courts. Rather, the specific features and acts described above are disclosed as example forms of implementing the claims.

What is claimed is:

1. A testing machine for testing a test specimen, the testing machine comprising:
   an actuator assembly configured to be coupled to the test specimen, the actuator assembly having a physical component; and
   a computing device configured to control the actuator assembly, wherein the computing device includes a graphical user interface that renders a simulated visual representation of the physical component and a simulated visual representation of a configurable parameter of the physical component that is configurable prior to operating the actuator assembly, wherein the simulated visual representation of the configurable parameter of the physical component includes a simulated visual representation of limits corresponding to actual limit values stored in a controller of the actuator assembly, wherein the simulated visual representation of limits is adjustable in the graphical user interface, and wherein the computing device controls the actuator assembly according to the limits.

2. The testing machine of claim 1 wherein the graphical user interface comprises multiple panel portions, a first panel portion having the simulated visual representations, and a second panel portion with activation elements having tasks for configuring the testing machine.

3. The testing machine of claim 2 wherein the second panel portion renders categories of tasks to configure the testing machine, and wherein the graphical user interface comprises a third panel portion, the third panel portion providing information indicative of tasks performed in each of the categories of tasks.

4. The testing machine of claim 3 wherein the physical component is a first physical component, and wherein the first panel portion comprises a second simulated visual representation of a second physical component of the testing machine, the second simulated visual representation be separate from a first simulated visual representation of the first physical component, the second simulated visual representation having a scale indicative of a parameter of the second physical component.

5. The testing machine of claim 1 wherein the simulated visual representation of the physical component includes a photographic image of at least a part of the physical component and the simulated visual representation of the configurable parameter includes a photographic image of at least a part of the configurable parameter.

6. The testing machine of claim 5 wherein the photographic image is manipulable to simulate motion.

7. The testing machine of claim 1 wherein the simulated visual representation of the physical component includes a graphical representation of at least a part of the physical component, and wherein the graphical representation is manipulable to simulate motion.

8. The testing machine of claim 2 wherein the second panel portion includes a guide that provides navigation for a user to set up the testing machine, wherein the guide lists the tasks for configuring the testing machine.

9. A testing machine for testing a test specimen, the testing machine comprising:
an actuator assembly configured to be coupled to the test specimen; and
a computing device configured to control the actuator assembly, wherein the computing device includes a graphical user interface rendering a simulated visual representation of the testing machine on a first portion of the graphical user interface,
wherein the graphical interface includes a second portion spaced apart from the first portion,
wherein the second portion includes a guide that provides navigation for a user to set up the testing machine,
wherein the guide lists a plurality of tasks for configuring the testing machine prior to operating the testing machine,
wherein the simulated visual representation of the testing machine includes a simulated visual representation of limits corresponding to actual limit values stored in a controller of the actuator assembly,
wherein the simulated visual representation of limits is adjustable in the graphical user interface, and
wherein the computing device controls the actuator assembly according to the limit.

10. The testing machine of claim 9 and further comprising a third portion of the graphical user interface separate from both the first portion and the second portion, the third portion rendering information indicative of different tasks listed in the second portion.

11. The testing machine of claim 9 wherein the simulated visual representation of the testing machine includes a photographic image of at least a part of the testing machine.

12. The testing machine of claim 9 wherein the simulated visual representation of the testing machine includes a graphical representation of at least a part of the testing machine, and wherein the graphical representation is manipulable to simulate motion.

13. A testing machine comprising:
an actuator;
a fixture configured to engage a test specimen to conduct a test; and
a controller configured to:
control the actuator, and
access a storage device having information related to operating parameters of the actuator and information related to operating parameters of the fixture, and
the controller having a graphical user interface to visually render a simulated relative location of the parameters of the fixture with respect to location of the parameters of the actuator, wherein at least some tasks used to configure the testing machine prior to operating the testing machine are graphically represented in the graphical user interface,
wherein the simulated relative location of the parameters of the actuator includes a simulated visual representation of limits corresponding to actual limit values stored in the controller,
wherein the simulated visual representation of limits is adjustable in the graphical user interface, and
wherein the controller controls the actuator according to the limits of the actuator.

14. The testing machine of claim 13 wherein the visual representation of limits on the graphical user interface for the fixture are inhibited from exceeding the parameters of the actuator.

15. A testing machine for testing a test specimen, the testing machine comprising:
an actuator assembly configured to be coupled to the test specimen, the actuator assembly having a physical component and a moving part; and
a computing device configured to control the actuator assembly,
wherein the computing device includes a graphical user interface that renders a simulated visual representation of the physical component and a simulated visual representation of the moving part,
wherein the simulated visual representation of the moving part includes a simulated visual representation of limits corresponding to actual limit values of the moving part stored in a controller of the actuator assembly, wherein the simulated visual representation of limits is adjustable in the graphical user interface, wherein the simulated visual representation of the moving part moves in accordance with actual movement of the moving part of the actuator assembly, wherein a parameter associated with the moving part is configurable through the graphical user interface such that the moving part is controlled at least partially through the graphical user interface, and wherein at least some tasks used to configure the testing machine prior to operating the testing machine are graphically represented in the simulated visual representation of the physical component.

16. The testing machine of claim 15 wherein at least some parameters of the control of the actuator assembly by the computing device are graphically represented in the graphical user interface.

17. The testing machine of claim 16 wherein the at least some parameters of the control of the actuator assembly by the computing device are configurable on the graphical user interface.

18. The testing machine of claim 15 wherein at least some parameters of the control of the actuator assembly by the computing device are configurable on the graphical user interface.

19. The testing machine of claim 16 wherein the graphical user interface comprises multiple panel portions, a first panel portion showing the moving part of the actuator assembly, and a second panel portion having the at least some parameters of the control of the actuator assembly.

20. The testing machine of claim 15 wherein the simulated visual representation of the physical component includes a photographic image of at least a part of the physical component and the simulated visual representation of the moving part includes a photographic image of at least a part of the moving part.

21. The testing machine of claim 15 wherein the simulated visual representation includes a graphical representation of the physical component or the moving part of the actuator assembly, and wherein the graphical representation is manipulable to simulate motion.

22. The testing machine of claim 15 wherein a graphical indicator in the graphical user interface is of similar shape to an indicator provided on the testing machine and perceivable aspects of the graphical indicator change in the same fashion as the indicator provided on the testing machine so as to indicate an operational state of the testing machine.

23. The testing machine of claim 15 wherein the graphical user interface provides a graphical element for specifying a first direction or representative force in the simulated visual representation of the moving part that shows positive values and a second direction or representative force in the simulated visual representation of the moving part that shows negative values.

24. The testing machine of claim 15 wherein the graphical user interface includes multiple graphical feedback indicators corresponding to multiple channels of data provided by respective sensors sensing different physical states of the physical component.

25. The testing machine of claim 15 wherein the graphical user interface includes multiple graphical feedback indicators corresponding to multiple channels of data provided by respective sensors sensing different physical states of the moving part.

* * * * *